US007674891B2

(12) United States Patent
Gravina et al.

(10) Patent No.: US 7,674,891 B2
(45) Date of Patent: Mar. 9, 2010

(54) NUCLEIC ACID MOLECULES ENCODING GPR84

(75) Inventors: Stephen Anthony Gravina, Rutherford, NJ (US); Jason M. Montez, Rumson, NJ (US); Hailin Wang, East Brunswick, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/184,368

(22) Filed: Aug. 1, 2008

(65) Prior Publication Data

US 2010/0028929 A1 Feb. 4, 2010

(51) Int. Cl.
*C07H 21/02* (2006.01)
*C07H 21/04* (2006.01)
*C12P 21/06* (2006.01)
*C12N 1/20* (2006.01)
*C12N 15/00* (2006.01)
*C12N 5/00* (2006.01)
*C12N 5/02* (2006.01)
*C12N 15/74* (2006.01)

(52) U.S. Cl. .................. 536/23.1; 435/69.1; 435/252.3; 435/320.1; 435/325; 435/471

(58) Field of Classification Search .................. None
See application file for complete search history.

(56) References Cited

U.S. PATENT DOCUMENTS

2007/0196867 A1  8/2007  Mancebo et al. ............. 435/7.2

FOREIGN PATENT DOCUMENTS

WO     WO 2007/027661       3/2007

OTHER PUBLICATIONS

Matsumura et al., "GPR expression in the rat taste bud relating to fatty acid sensing", Biomedical Research 2007 28(1):49-55.
Perroy et al., "The C terminus of the metabotropic glutamate receptor subtypes 2 and 7 specifies the receptor signaling pathways", J Biol Chem 2001 276(49):45800-45805.
Parmentier et al., "The G protein-coupling profile of metabotropic glutamate receptors, as determined with exogenous G proteins, independent of their ligand recognition domain", Molecular Pharmacology 1998 53:778-786.

Wang et al., "Medium-chain fatty acids as ligands for Orphan G protein-coupled receptor GPR84", J Biol Chem 2006 281(45):34457-34464.
Milligan, G., "Strategies to identify ligands for orphan G-protein-coupled receptors", Biochemical Society Transactions 2002 30(4):789-793.
NCBI Accession No. NP_065103 [gi:9966839] with Revision History, Sep. 5, 2000-Feb. 10, 2008.
NCBI Accession No. NM_020370 [gi:9966838] with Revision History, Sep. 5, 2000-Feb. 10, 2008.
NCBI Accession No. NP 109645 [gi:13507672] with Revision History, Apr. 2, 2001-Feb. 11, 2008.
NCBI Accession No. NM_030720 [gi:13507671] with Revision History, Apr. 2, 2001-Feb. 11, 2008.
NCBI Accession No. NP_001102979 [gi:157824113] with Revision History, Oct. 3, 2007-Apr. 29, 2008.
NCBI Accession No. NM_001109509 [gi:157824112] with Revision History, Oct. 3, 2007-Apr. 29, 2008.
NCBI Accession No. NP_001033657 [gi:84370179] with Revision History, Jan. 5, 2006-Jun. 27, 2007.
NCBI Accession No. NM_001038568 [gi:84370178] with Revision History, Jan. 5, 2006-Jun. 27, 2007.
NCBI Accession No. NP_002063 [gi:40254462] with Revision History, Mar. 19, 1999-Jun. 22, 2008.
NCBI Accession No. NM_002072 [gi:40254461] with Revision History, Mar. 19, 1999-Jun. 22, 2008.
NCBI Accession No. NP_032165 [gi:84662745] with Revision History, Jan. 4, 2000-Aug. 24, 2008.
NCBI Accession No. NM_008139 [gi:145966786] with Revision History, Jan. 4, 2000-Oct. 12, 2008.
NCBI Accession No. NP_112298 [gi:13591957] with Revision History, Apr. 11, 2001-Sep. 14, 2008.
NCBI Accession No. NM_031036 [gi:13591956] with Revision History, Apr. 11, 2001-Sep. 14, 2008.
NCBI Accession No. NP_001001547 [gi:48375176] with Revision History, Jun. 4, 2004-Sep. 14, 2008.
NCBI Accession No. NP_031669 [gi:31982474] with Revision History, Jan. 4, 2000-Aug. 3, 2008.
NCBI Accession No. NP_113749 [gi:48675379] with Revision History, May 2, 2001-Sep. 13, 2008.
NCBI Accession No. NM_007643 [gi:142363407] with Revision History, Jan. 4, 2000-Aug. 3, 2008.
NCBI Accession No. NM_031561 [gi:48675378] with Revision History, May 2, 2001-Sep. 13, 2008.

*Primary Examiner*—Robert Landsman
(74) *Attorney, Agent, or Firm*—Licata & Tyrrell P.C.

(57) ABSTRACT

The present invention is an isolated nucleic acid molecule encoding CD36, $G_{qi9}$, and G protein-coupled receptor 84 (GPR84) proteins as well as vectors and recombinant host cells which co-express CD36, $G_{qi9}$, and GPR84 proteins for use in identifying modulators of GPR84 activity.

5 Claims, No Drawings

SEQUENCE LISTING

```
<160> NUMBER OF SEQ ID NOS: 22

<210> SEQ ID NO 1
<211> LENGTH: 396
<212> TYPE: PRT
<213> ORGANISM: Homo sapiens

<400> SEQUENCE: 1

Met Trp Asn Ser Ser Asp Ala Asn Phe Ser Cys Tyr His Glu Ser Val
1               5                   10                  15

Leu Gly Tyr Arg Tyr Val Ala Val Ser Trp Gly Val Val Val Ala Val
                20                  25                  30

Thr Gly Thr Val Gly Asn Val Leu Thr Leu Leu Ala Leu Ala Ile Gln
            35                  40                  45

Pro Lys Leu Arg Thr Arg Phe Asn Leu Leu Ile Ala Asn Leu Thr Leu
        50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Thr Phe Cys Arg Val Phe
                85                  90                  95

Gly Leu Leu Leu Phe Ala Ser Asn Ser Val Ser Ile Leu Thr Leu Cys
                100                 105                 110

Leu Ile Ala Leu Gly Arg Tyr Leu Leu Ile Ala His Pro Lys Leu Phe
            115                 120                 125

Pro Gln Val Phe Ser Ala Lys Gly Ile Val Leu Ala Leu Val Ser Thr
        130                 135                 140

Trp Val Val Gly Val Ala Ser Phe Ala Pro Leu Trp Pro Ile Tyr Ile
145                 150                 155                 160

Leu Val Pro Val Val Cys Thr Cys Ser Phe Asp Arg Ile Arg Gly Arg
                165                 170                 175

Pro Tyr Thr Thr Ile Leu Met Gly Ile Tyr Phe Val Leu Gly Leu Ser
                180                 185                 190
```

```
Ser Val Gly Ile Phe Tyr Cys Leu Ile His Arg Gln Val Lys Arg Ala
        195                 200                 205
Ala Gln Ala Leu Asp Gln Tyr Lys Leu Arg Gln Ala Ser Ile His Ser
    210                 215                 220
Asn His Val Ala Arg Thr Asp Glu Ala Met Pro Gly Arg Phe Gln Glu
225                 230                 235                 240
Leu Asp Ser Arg Leu Ala Ser Gly Gly Pro Ser Glu Gly Ile Ser Ser
                245                 250                 255
Glu Pro Val Ser Ala Ala Thr Thr Gln Thr Leu Glu Gly Asp Ser Ser
            260                 265                 270
Glu Val Gly Asp Gln Ile Asn Ser Lys Arg Ala Lys Gln Met Ala Glu
        275                 280                 285
Lys Ser Pro Pro Glu Ala Ser Ala Lys Ala Gln Pro Ile Lys Gly Ala
    290                 295                 300
Arg Arg Ala Pro Asp Ser Ser Glu Phe Gly Lys Val Thr Arg Met
305                 310                 315                 320
Cys Phe Ala Val Phe Leu Cys Phe Ala Leu Ser Tyr Ile Pro Phe Leu
                325                 330                 335
Leu Leu Asn Ile Leu Asp Ala Arg Val Gln Ala Pro Arg Val Val His
            340                 345                 350
Met Leu Ala Ala Asn Leu Thr Trp Leu Asn Gly Cys Ile Asn Pro Val
        355                 360                 365
Leu Tyr Ala Ala Met Asn Arg Gln Phe Arg Gln Ala Tyr Gly Ser Ile
    370                 375                 380
Leu Lys Arg Gly Pro Arg Ser Phe His Arg Leu His
385                 390                 395

<210> SEQ ID NO 2
<211> LENGTH: 1546
<212> TYPE: DNA
<213> ORGANISM: Homo sapiens

<400> SEQUENCE: 2
taactgtcca ccagaaagga ctgctctttg ggtgagttga acttcttcca ttatagaaag     60
aattgaaggc tgagaaactc agcctctatc atgtggaaca gctctgacgc caacttctcc    120
tgctaccatg agtctgtgct gggctatcgt tatgttgcag ttagctgggg ggtggtggtg    180
gctgtgacag gcaccgtggg caatgtgctc accctactgg ccttggccat ccagcccaag    240
ctccgtaccc gattcaacct gctcatagcc aacctcacac tggctgatct cctctactgc    300
acgctccttc agcccttctc tgtggacacc tacctccacc tgcactggcg caccggtgcc    360
accttctgca gggtatttgg ctcctccttt ttgcctcca attctgtctc catcctgacc    420
ctctgcctca tcgcactggg acgctacctc ctcattgccc accctaagct tttccccaa    480
gttttcagtg ccaagggat agtgctggca ctggtgagca cctgggttgt gggcgtggcc    540
agctttgctc ccctctggcc tatttatatc ctggtacctg tagtctgcac ctgcagcttt    600
gaccgcatcc gaggccggcc ttacaccacc atcctcatgg gcatctactt tgtgcttggg    660
ctcagcagtg ttggcatctt ctattgcctc atccaccgcc aggtcaaacg agcagcacag    720
gcactggacc aatacaagtt gcgacaggca agcatccact ccaaccatgt ggccaggact    780
gatgaggcca tgcctggtcg tttccaggag ctggacagca ggttagcatc aggaggaccc    840
agtgagggga tttcatctga gccagtcagt gctgccacca cccagaccct ggaagggac    900
tcatcagaag tgggagacca gatcaacagc aagagagcta agcagatggc agagaaaagc    960
```

-continued

```
cctccagaag catctgccaa agcccagcca attaaaggag ccagaagagc tccggattct   1020
tcatcggaat ttgggaaggt gactcgaatg tgttttgctg tgttcctctg ctttgccctg   1080
agctacatcc ccttcttgct gctcaacatt ctggatgcca gagtccaggc tccccgggtg   1140
gtccacatgc ttgctgccaa cctcacctgg ctcaatggtt gcatcaaccc tgtgctctat   1200
gcagccatga accgccaatt ccgccaagca tatggctcca ttttaaaaag agggccccgg   1260
agtttccata ggctccatta gaactgtgac cctagtcacc agaattcagg actgtctcct   1320
ccaggaccaa agtggccagg taataggaga ataggtgaaa taacacatgt gggcatttte   1380 acaacaatct ctccccagcc tcccaaatca agtctctcca tcacttgatc aatgtttcag   1440
ccctagactg cccaaggagt attattaatt attaataaat gaattctgtg cttttaaaaa   1500
aaaaaaaata aaaaagaaa aaaaaaaaaa aaaaaaaaaa aaaaaa                   1546
```

<210> SEQ ID NO 3
<211> LENGTH: 396
<212> TYPE: PRT
<213> ORGANISM: Mus musculus

<400> SEQUENCE: 3

```
Met Trp Asn Ser Ser Asp Ala Asn Phe Ser Cys Tyr His Glu Ser Val
1               5                   10                  15

Leu Gly Tyr Arg Tyr Phe Ala Ile Ile Trp Gly Val Ala Val Ala Val
            20                  25                  30

Thr Gly Thr Val Gly Asn Val Leu Thr Leu Leu Ala Leu Ala Ile Arg
        35                  40                  45

Pro Lys Leu Arg Thr Arg Phe Asn Leu Leu Ile Ala Asn Leu Thr Leu
    50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Val Phe Cys Arg Ile Phe
                85                  90                  95

Gly Leu Leu Leu Phe Thr Ser Asn Ser Val Ser Ile Leu Thr Leu Cys
            100                 105                 110

Leu Ile Ala Leu Gly Arg Tyr Leu Leu Ile Ala His Pro Lys Leu Phe
        115                 120                 125

Pro Gln Val Phe Ser Ala Lys Gly Ile Val Leu Ala Leu Val Gly Ser
    130                 135                 140

Trp Val Val Gly Val Thr Ser Phe Ala Pro Leu Trp Asn Val Phe Val
145                 150                 155                 160

Leu Val Pro Val Val Cys Thr Cys Ser Phe Asp Arg Met Arg Gly Arg
                165                 170                 175

Pro Tyr Thr Thr Ile Leu Met Gly Ile Tyr Phe Val Leu Gly Leu Ser
            180                 185                 190

Ser Val Gly Val Phe Tyr Cys Leu Ile His Arg Gln Val Lys Arg Ala
        195                 200                 205

Ala Arg Ala Leu Asp Gln Tyr Gly Leu His Gln Ala Ser Ile Arg Ser
    210                 215                 220

His Gln Val Ala Gly Thr Gln Glu Ala Met Pro Gly His Phe Gln Glu
225                 230                 235                 240

Leu Asp Ser Gly Val Ala Ser Arg Gly Pro Ser Glu Gly Ile Ser Ser
                245                 250                 255

Glu Pro Val Ser Ala Ala Thr Thr Gln Thr Leu Glu Gly Asp Ser Ser
            260                 265                 270
```

```
Glu Ala Gly Gly Gln Gly Ile Arg Lys Ala Ala Gln Gln Ile Ala Glu
            275                 280                 285

Arg Ser Leu Pro Glu Val His Arg Lys Pro Arg Glu Thr Ala Gly Ala
            290                 295                 300

Arg Arg Ala Thr Asp Ala Pro Ser Glu Phe Gly Lys Val Thr Arg Met
305                 310                 315                 320

Cys Phe Ala Val Phe Leu Cys Phe Ala Leu Ser Tyr Ile Pro Phe Leu
                325                 330                 335

Leu Leu Asn Ile Leu Asp Ala Arg Gly Arg Ala Pro Arg Val Val His
            340                 345                 350

Met Val Ala Ala Asn Leu Thr Trp Leu Asn Ser Cys Ile Asn Pro Val
            355                 360                 365

Leu Tyr Ala Ala Met Asn Arg Gln Phe Arg His Ala Tyr Gly Ser Ile
            370                 375                 380

Leu Lys Arg Gly Pro Gln Ser Phe Arg Arg Phe His
385                 390                 395

<210> SEQ ID NO 4
<211> LENGTH: 1611
<212> TYPE: DNA
<213> ORGANISM: Mus musculus

<400> SEQUENCE: 4
ttatatgtcc agctggaagc ctggctgtcc ctagaaaagc tggaagcctg actgcccctc      60
aaaagacctg ctctttagga gagctagata ttgtttactg aagacaagtg tgaaaactgg    120
gaacctcagt ctccatcatg tggaacagct cagatgccaa cttctcctgc taccatgagt    180
ctgtgttggg ctatcgatac tttgcaatta tctggggcgt ggcagtggct gtgacaggca    240
cggtgggcaa tgtgctcact ctgctggcct tggccattcg tcccaagctc cgaacccgct    300
tcaacctgct cattgccaac ctcacccctgg ctgatctact ctactgcacg ctcctgcagc    360 cttttctccgt ggacacatac ctccacctcc attggcgtac cggcgcggtc ttctgtagaa    420
tatttggact cctcctcttt acttccaatt ctgtctccat cctcaccctc tgtctcattg    480
ctctaggacg ctacctcctc attgcccacc ctaagctctt tccccaggtt ttcagtgcca    540
aggggatcgt gctggcactg gtgggcagct gggttgtggg ggtgaccagc tttgcccccc    600 tctgaatgt ttttgtcttg gtgccagttg tctgcacttg cagcttgac cgcatgcgag    660 gccggcctta caccaccatc ctcatgggca tctactttgt gcttggctc agcagcgtgg    720 gcgtcttcta ctgcctcatc caccggcaag tgaagcgtgc ggctcgagca ctggaccaat    780
acgggctgca tcaggccagc atccgctctc atcaggtggc tgggacacaa gaagccatgc    840
ctggccactt ccaggagcta gacagcgggg ttgcctcaag agggcccagc gagggggattt    900 catctgagcc agtcagtgct gcgaccacgc agaccctgga aggtgattcg tcagaagctg    960
ggggccaggg cattagaaag gcagctcaac agatcgcaga gagaagcctt ccagaagtgc    1020
atcgcaagcc ccgggaaact gcaggagctc gcagagccac agatgcccca tcagagttcg    1080
ggaaggtgac ccgtatgtgc ttcgcagtgt tcctctgctt cgccctcagc tacatcccct    1140
tcctgttgct caacattctg gacgccaggg gccgtgctcc acgagtagtg cacatggtgg    1200
ctgccaacct cacctggctc aacagctgca tcaaccctgt gctctatgca gccatgaacc    1260 gccagttttcg ccacgcgtat ggctccatcc tgaaacgcgg gccacagagt tccgccggt    1320 tccattaaag ctatttaaag ctagtagtcc attcaccagg acaggccaaa catccggaac    1380
cagagtggcc tgcagaggac aggacaggag cccttcagtc cttgggtatt tcacagacaa    1440
```

```
cctcagtggt atagaggtac accactttcc cattcaggaa tcagtgcgtc aaccctgtgt    1500
gacccaagga gtgtggttaa ttattaataa agacattgca tccccccctc aaaaaaaaaa    1560
aaaaaaaaaa aaaaaaaaaa aaaaaaaaaa aaaaaaaaaa aaaaaaaaaa a             1611
```

<210> SEQ ID NO 5
<211> LENGTH: 396
<212> TYPE: PRT
<213> ORGANISM: Rattus norvegicus

<400> SEQUENCE: 5

```
Met Trp Asn Ser Ser Asp Asp Asn Phe Ser Cys Tyr His Glu Ser Val
1               5                   10                  15

Leu Gly Tyr Arg Tyr Phe Ala Val Ile Trp Gly Met Val Val Ala Ala
                20                  25                  30

Thr Gly Thr Val Gly Asn Val Leu Thr Leu Leu Ala Leu Ala Ile Arg
            35                  40                  45

Pro Lys Leu Arg Thr Arg Phe Asn Leu Leu Ile Ala Asn Leu Thr Leu
        50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Ile Phe Cys Arg Ile Phe
                85                  90                  95

Gly Leu Leu Leu Phe Thr Ser Asn Ser Val Ser Ile Leu Thr Leu Cys
                100                 105                 110

Leu Ile Ala Leu Gly Arg Tyr Leu Leu Ile Ala His Pro Lys Leu Phe
            115                 120                 125

Pro Gln Val Phe Ser Ala Lys Gly Ile Val Leu Ala Leu Val Gly Ser
        130                 135                 140

Trp Val Val Gly Val Thr Ser Phe Ala Pro Leu Trp Asn Val Tyr Val
145                 150                 155                 160

Leu Val Pro Val Val Cys Thr Cys Ser Phe Asp Arg Val Arg Gly Arg
                165                 170                 175

Pro Tyr Thr Thr Ile Leu Met Gly Ile Phe Phe Val Val Gly Leu Ser
                180                 185                 190

Ser Val Gly Val Phe Tyr Cys Leu Ile His Arg Gln Val Lys Arg Ala
            195                 200                 205

Ala Arg Ala Leu Asp Lys Tyr Gly Leu Gln Glu Ala Ser Met Arg Ser
        210                 215                 220

His Gln Val Ser Gly Thr His Glu Ala Val Pro Gly His Phe Gln Glu
225                 230                 235                 240

Leu Asp Ser Gly Leu Ala Ser Arg Gly Pro Ser Glu Gly Ile Ser Ser
                245                 250                 255

Glu Pro Val Ser Ala Ala Thr Thr Gln Thr Leu Glu Gly Asp Ser Ser
                260                 265                 270

Glu Ala Gly Asp Gln Gly Met Arg Lys Ala Ala Gln Ile Ser Glu
            275                 280                 285

Arg Ser Leu Pro Glu Val His Arg Lys Thr Gly Gly Ala Ala Gly Ala
        290                 295                 300

Arg Arg Ala Thr Asp Ala Pro Ser Glu Phe Gly Lys Val Thr Arg Met
305                 310                 315                 320

Cys Phe Ala Val Phe Leu Cys Phe Val Leu Ser Tyr Ile Pro Phe Leu
                325                 330                 335

Leu Leu Asn Ile Leu Asp Ala Arg Gly Arg Ala Pro Arg Val Val His
                340                 345                 350
```

Met Val Ala Ala Asn Leu Thr Trp Leu Asn Ser Cys Ile Asn Pro Val
        355                 360                 365

Leu Tyr Ala Ala Met Asn Arg Gln Phe Arg Gln Ala Tyr Gly Ser Ile
    370                 375                 380

Leu Lys Arg Gly Pro Gln Ser Phe Arg Arg Phe His
385                 390                 395

<210> SEQ ID NO 6
<211> LENGTH: 1493
<212> TYPE: DNA
<213> ORGANISM: Rattus norvegicus

<400> SEQUENCE: 6

| | | | | | |
|---|---|---|---|---|---|
| ttatatgtcc | agctgaaagc | ctggctgtcc | ctcaaaaggc | atgctcttta ggtgagctag | 60 |
| atattgttta | ctgaagacaa | gtgtgaaaac | tgggaacctc | aggtgagtct ccatcatgtg | 120 |
| gaacagctca | gatgacaact | tctcctgcta | ccatgagtct | gtattgggct atcgatactt | 180 |
| tgcagttatc | tggggcatgg | tagtggctgc | aacaggcacc | gtgggcaatg tgctcaccct | 240 |
| gttggccttg | ccatccgtc  | ccaaactccg | aacccgtttc | aacctgctca ttgccaacct | 300 |
| caccctggct | gatctactct | actgcacgct | cctgcagcct | ttctccgtgg acacatacct | 360 |
| ccacctccat | tggcgcaccg | cgccatcttc | tgtagaata  | ttcggactcc tcctctttac | 420 |
| ttccaattct | gtctccattc | ttaccctctg | tctcattgct | ctaggacgct accttctcat | 480 |
| tgcccaccct | aagctctttc | cccaggtttt | cagtgccaag | gggatcgtgc tggcactagt | 540 |
| gggcagctgg | gttgtggggg | tgaccagctt | tgccccctc  | tggaatgttt atgtcttggt | 600 |
| gccagttgtc | tgcacctgca | gctttgaccg | cgtgcgaggc | cggccttaca ccaccatcct | 660 |
| catgggcatc | ttctttgtgg | ttgggctcag | cagcgtgggc | gtcttctact gcctcatcca | 720 |
| ccgccaagtg | aagcgtgcgg | ctcgagcgct | ggacaaatat | gggctgcagg aggccagcat | 780 |
| gcgctcccat | caggtgtctg | ggacacatga | agctgtgcca | ggccacttcc aggagctaga | 840 |
| cagcgggctt | gcatcaagag | gtcccagcga | agggatttca | tctgagccag tcagtgctgc | 900 |
| gacgacacag | accctggaag | gtgattcgtc | agaagcgggg | gaccagggca tgagaaaggc | 960 |
| agctcagcag | atctcagaga | gaagccttcc | agaagtgcat | cgcaagactg aggagctgc  | 1020 |
| aggagcacgc | agagccacgg | atgcaccatc | ggagttcggg | aaggtgaccc gtatgtgctt | 1080 |
| tgcagtgttc | ctttgcttcg | tcctcagcta | catcccttc  | ctgctgctca acattctgga | 1140 |
| cgccaggggc | cgcgctccac | gagtagtgca | tatggttgct | gccaacctca cctggctcaa | 1200 |
| cagctgcatc | aaccctgtgc | tctatgcagc | catgaaccgc | cagtttcgcc aggcttatgg | 1260 |
| ctccatcctg | aaacgcgggc | cacagagttt | ccgacggttc | cattagagct agtagtccac | 1320 |
| tcaccaggcc | aggtcaaacg | agaaccgag  | tggcctgcag | aggacaggat aagagcccct | 1380 |
| cacatttcac | agacaacctc | agtggtatag | aggtacaccg | tttccccact caggaatcag | 1440 |
| tgtgccaacc | ctgtgtgacc | caaggaatgt | ggttattaat | aaacacattg cat | 1493 |

<210> SEQ ID NO 7
<211> LENGTH: 396
<212> TYPE: PRT
<213> ORGANISM: Bos taurus

```
<400> SEQUENCE: 7

Met Trp Asn Ala Ser Asp Val Asn Phe Ser Cys Tyr His Glu Ser Val
1               5                   10                  15

Leu Gly Tyr Arg Tyr Val Ala Val Ser Trp Gly Ile Val Val Ala Val
            20                  25                  30

Thr Gly Thr Val Gly Asn Val Leu Thr Leu Leu Ala Leu Ala Ile Gln
        35                  40                  45

Pro Lys Leu Arg Thr Arg Phe Asn Leu Leu Ile Ala Asn Leu Thr Val
    50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Thr Phe Cys Gln Ile Phe
                85                  90                  95

Gly Phe Leu Leu Phe Val Ser Asn Ser Val Ser Ile Leu Thr Leu Cys
            100                 105                 110

Leu Ile Ala Leu Gly Arg Tyr Leu Leu Ile Ala His Pro Lys Leu Phe
            115                 120                 125

Pro Gln Val Phe Ser Ala Lys Gly Met Val Leu Ala Leu Val Ser Thr
    130                 135                 140

Trp Val Val Ala Val Ala Ser Phe Ala Pro Leu Trp Pro Ile Tyr Ile
145                 150                 155                 160

Leu Val Pro Val Val Cys Thr Cys Ser Phe Asp Arg Ile Arg Gly Gln
                165                 170                 175

Pro Tyr Thr Thr Ile Leu Met Gly Ile Tyr Phe Val Val Gly Leu Ser
            180                 185                 190

Ser Val Gly Val Phe Tyr Cys Leu Ile His Gln Val Lys Arg Ala
            195                 200                 205

Ala Gln Ala Leu Asn Gln Tyr Lys Leu Arg Gln Ala Ser Ile Arg Ser
    210                 215                 220

Asn His Val Ala Gly Ala His Glu Ala Val Pro Gly Arg Phe Gln Glu
225                 230                 235                 240

Leu Asp Ser Gly Leu Ala Ser Gly Gly Pro Ser Glu Gly Ile Ser Ser
            245                 250                 255

Glu Pro Val Ser Ala Ala Thr Thr Gln Thr Leu Glu Gly Asp Ser Ser
            260                 265                 270

Glu Val Arg Asp Gln Ser Ser Lys Ala Ala Lys Gln Met Ala Glu
            275                 280                 285

Lys Asn Pro Pro Gly Val Ala Ala Lys Ala Arg Thr Thr Lys Gly Ala
    290                 295                 300

Gln Arg Ala Gln Asp Ser Pro Ser Glu Phe Gly Lys Val Thr Arg Met
305                 310                 315                 320

Cys Phe Ala Val Phe Leu Cys Phe Thr Leu Ser Tyr Ile Pro Phe Leu
                325                 330                 335

Leu Leu Asn Ile Leu Asp Ala Lys Val Gln Ala Pro Arg Val Val His
            340                 345                 350

Met Leu Ala Ala Asn Leu Thr Trp Leu Asn Gly Cys Ile Asn Pro Val
            355                 360                 365

Leu Tyr Ala Ala Met Asn Arg Gln Phe Arg Gln Ala Tyr Gly Ser Leu
    370                 375                 380

Leu Arg Arg Gly Pro Gln Ser Phe His Arg Phe His
385                 390                 395
```

<210> SEQ ID NO 8
<211> LENGTH: 1485
<212> TYPE: DNA
<213> ORGANISM: Bos taurus

<400> SEQUENCE: 8

```
aaaggactat gctttgagtg agttgaacgt cttccgctga agagagattt gaaggctagg      60
agactcagct tccatcatgt ggaacgcttc tgacgtcaac ttctcctgct accatgagtc     120
tgtgctgggc tatcgttacg tggcagttag ctggggaatt gtggtggccg tgacgggcac     180
ggtgggcaac gtgctcaccc tgctggcctt ggccatccag cccaagctcc gaacccgctt     240
caacctgctc atcgccaacc tcacagtggc tgatctgctc tattgcaccc ttctccagcc     300
cttctcggtg gacacctacc tccacctgca ctggcgcacc ggtgccacct tctgccagat     360
cttttggggttc ctccttttttg tatccaactc tgtctccatc ctcaccctct gcctcatcgc     420
cctggggcgc tatctcctca ttgcccaccc taagctcttt ccccaagttt tcagtgccaa     480
gggcatggtg ctggcactgg tgagcacctg ggtggtggct gtggccagct cgctcccct     540
ctggccaatc tatatcttgg tgcccgtagt ctgcacttgc agctttgatc gcatccgagg     600
ccagccctac accaccatcc tcatgggcat ctattttgtg gttgggctca gcagtgtcgg     660
tgtcttctat tgcctcatcc accagcaggg gaagcgagca gcacaggcac tgaatcagta     720
caagctgcgc caggcaagca tccgttccaa ccatgtggct ggggcacacg aggccgtgcc     780
tggtcgtttc caggagctag acagtgggct ggcatcagga ggaccagcg aggggatttc     840
atctgagcca gtcagtgctg ccaccaccca gaccctggaa ggagactcat cagaagtcag     900
ggaccagagc tccagtaagg cagctaagca gatggcagag aaaaaccctc caggagtggc     960
tgccaaggcc aggacaacta aaggagccca gagagctcag gactctccat cagagtttgg    1020
gaaggtaacc cggatgtgtt ttgctgtgtt cctctgcttc accctgagct acatcccttt    1080
cttgctactc aacatcctgg atgccaaggt ccaggctccc cgagttgtcc acatgctcgc    1140
tgccaacctc acctggctta atggctgcat caaccctgtg ctgtacgcag ccatgaaccg    1200
ccagttccgc caagcctacg gctccctcct gagacgaggg ccccagagtt tccataggtt    1260
ccattaaaac tgtgtcccca gtcaccagaa tctgggattg tctcttccag aactaaggtg    1320
gccagctgtt ataggaatag gtgaaagtga gatctgtggg aattttcatg gacaaccacc    1380
cctcaaactt cccaaacccg gcctctccac gcttcactca acatttcagc cctaggctgc    1440
tcaagatgca ttattaatta ttaataaatg aattctatcc tcttc                    1485
```

<210> SEQ ID NO 9
<211> LENGTH: 1191
<212> TYPE: DNA
<213> ORGANISM: Homo sapiens

<400> SEQUENCE: 9

```
atgtggaaca gctctgacgc caacttctcc tgctaccatg agtctgtgct gggctatcgt     60
tatgttgcag ttagctgggg ggtggtggtg gctgtgacag gcaccgtggg caatgtgctc    120
accctactgg ccttggccat ccagcccaag ctccgtaccc gattcaacct gctcatagcc    180
aacctcacac tggctgatct cctctactgc acgctccttc agcccttctc tgtggacacc    240
tacctccacc tgcactggcg caccggtgcc accttctgca gggtatttgg gctcctcctt    300
tttgcctcca attctgtctc catcctgacc ctctgcctca tcgcactggg acgctacctc    360
ctcattgccc accctaagct ttttcccca gttttcagtg ccaagggat agtgctggca    420
```

```
ctggtgagca cctgggttgt gggcgtggcc agctttgctc ccctctggcc tatttatatc    480
ctcgtacctg tagtctgcac ctgcagcttt gaccgcatcc gaggccggcc ttacaccacc    540
atcctcatgg gcatctactt tgtgcttggg ctcagcagtg ttggcatctt ctattgcctc    600
atccaccgcc aggtcaaacg agcagcacag gcactggacc aatacaagtt gcgacaggca    660
agcatccact ccaaccatgt ggccaggact gatgaggcca tgcctggtcg tttccaggag    720
ctggacagca ggttagcatc aggaggaccc agtgagggga tttcatctga gccagtcagt    780
gctgccacca cccagaccct ggaaggggac tcatcagaag tgggagacca gatcaacagc    840
aagagagcta agcagatggc agagaaaagc cctccagaag catctgccaa agcccagcca    900
attaaaggag ccagaagagc tccggattct tcatcggaat tgggaaggt gactcgaatg    960
tgttttgctg tgttcctctg ctttgccctg agctacatcc ccttcttgct gctcaacatt   1020
ctggatgcca gagtccaggc tccccgggtg gtccacatgc ttgctgccaa cctcacctgg   1080
ctcaatggtt gcatcaaccc tgtgctctat gcagccatga accgccaatt ccgccaagca   1140
tatggctcca ttttaaaaag agggccccgg agtttccata ggctccatta g            1191
```

<210> SEQ ID NO 10
<211> LENGTH: 359
<212> TYPE: PRT
<213> ORGANISM: Homo sapiens

<400> SEQUENCE: 10

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240
```

-continued

```
Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 11
<211> LENGTH: 9
<212> TYPE: PRT
<213> ORGANISM: Homo sapiens

<400> SEQUENCE: 11

Asn Asn Leu Lys Asp Cys Gly Leu Phe
1               5

<210> SEQ ID NO 12
<211> LENGTH: 2188
<212> TYPE: DNA
<213> ORGANISM: Homo sapiens

<400> SEQUENCE: 12
agggggtgcc ggcggggctg cagcggaggc actttggaag aatgactctg gagtccatca      60
tggcgtgctg cctgagcgag gaggccaagg aagcccggcg gatcaacgac gagatcgagc     120
ggcagctccg cagggacaag cgggacgccc gccgggagct caagctgctg ctgctcggga     180
caggagagag tggcaagagt acgtttatca agcagatgag aatcatccat gggtcaggat     240
actctgatga agataaaagg ggcttcacca agctggtgta tcagaacatc ttcacggcca     300
tgcaggccat gatcagagcc atggacacac tcaagatccc atacaagtat gagcacaata     360
aggctcatgc acaattagtt cgagaagttg atgtggagaa ggtgtctgct tttgagaatc     420
catatgtaga tgcaataaag agtttatgga tgatcctgg aatccaggaa tgctatgata     480
gacgacgaga atatcaatta tctgactcta ccaaatacta tcttaatgac ttggaccgcg     540
tagctgaccc tgcctacctg cctacgcaac aagatgtgct tagagttcga gtccccacca     600
cagggatcat cgaatacccc tttgacttac aaagtgtcat tttcagaatg gtcgatgtag     660
ggggccaaag gtcagagaga agaaaatgga tacactgctt tgaaaatgtc acctctatca     720
tgtttctagt agcgcttagt gaatatgatc aagttctcgt ggagtcagac aatgagaacc     780
gaatggagga aagcaaggct ctctttagaa caattatcac ataccctgg ttccagaact     840 cctcggttat tctgttctta aacaagaaag atcttctaga ggagaaaatc atgtattccc     900
atctagtcga ctacttccca gaatatgatg gaccccagag agatgcccag gcagcccgag     960
aattcattct gaagatgttc gtggacctga acccagacag tgacaaaatt atctactccc    1020
acttcacgtg cgccacagac accgagaata tccgctttgt ctttgctgcc gtcaaggaca    1080
```

-continued

```
ccatcctcca gttgaacctg aaggagtaca atctggtcta attgtgcctc ctagacaccc    1140
gccctgccct tccctggtgg gctattgaag atacacaaga gggactgtat ttctgtggaa    1200
aacaatttgc ataatactaa tttattgccg tcctggactc tgtgtgagcg tgtccacaga    1260
gtttgtagta aatattatga ttttatttaa actattcaga ggaaaaacag aggatgctga    1320
agtacagtcc cagcacattt cctctctatc ttttttttag gcaaaacctt gtgactcagt    1380
gtattttaaa ttctcagtca tgcactcaca aagataagac ttgtttcttt ctgtctctct    1440
ctcttttcct tttctatgga gcaaaacaaa gctgatttcc cttttttctt ccccgctaa     1500
ttcataccct cctcctgatg ttttcccag gttacaatgg cctttatcct agttccattc     1560
ttggtcaagt ttttctctca atgatacag tcaggacaca tcgttcgatt taagccatca     1620
tcagcttaat ttaagtttgt agttttgct gaaggattat atgtattaat acttacggtt      1680
ttaaatgtgt tgctttggat acacacatag tttctttttt aatagaatat actgtcttgt    1740
ctcactttgg actgggacag tggatgccca tctaaaagtt aagtgtcatt tcttttagat    1800
gtttaccttc agccatagct tgattgctca gagaaatatg cagaaggcag atcaaagac     1860
acacaggagt cctttctttt gaaatgccac gtgccattgt cttccctccc ttctttgctt    1920
cttttcctta ccctctcttt caattgcaga tgccaaaaaa gatgccaaca gacactacat    1980
taccctaatg gctgctaccc agaaccttt tataggttgt tcttaatttt tttgttgttg    2040
ttgttcaagc ttttccttt tttttttct tagtgtttgg gccacgatt taaaatgact        2100
tttattatgg gtatgtgttg ccaaagctgg cttttttgtca aataaaatga atacgaactt   2160
aaaaaataaa aaaaaaaaa aaaaaaa                                          2188
```

<210> SEQ ID NO 13
<211> LENGTH: 359
<212> TYPE: PRT
<213> ORGANISM: Mus musculus

<400> SEQUENCE: 13

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175
```

-continued

```
Gln Asp Val Leu Arg Val Arg Val Pro Thr Thr Gly Ile Ile Glu Tyr
            180                 185                 190
Pro Phe Asp Leu Gln Ser Val Ile Phe Arg Met Val Asp Val Gly Gly
        195                 200                 205
Gln Arg Ser Glu Arg Arg Lys Trp Ile His Cys Phe Glu Asn Val Thr
    210                 215                 220
Ser Ile Met Phe Leu Val Ala Leu Ser Glu Tyr Asp Gln Val Leu Val
225                 230                 235                 240
Glu Ser Asp Asn Glu Asn Arg Met Glu Glu Ser Lys Ala Leu Phe Arg
                245                 250                 255
Thr Ile Ile Thr Tyr Pro Trp Phe Gln Asn Ser Ser Val Ile Leu Phe
            260                 265                 270
Leu Asn Lys Lys Asp Leu Leu Glu Glu Lys Ile Met Tyr Ser His Leu
        275                 280                 285
Val Asp Tyr Phe Pro Glu Tyr Asp Gly Pro Gln Arg Asp Ala Gln Ala
    290                 295                 300
Ala Arg Glu Phe Ile Leu Lys Met Phe Val Asp Leu Asn Pro Asp Ser
305                 310                 315                 320
Asp Lys Ile Ile Tyr Ser His Phe Thr Cys Ala Thr Asp Thr Glu Asn
                325                 330                 335
Ile Arg Phe Val Phe Ala Ala Val Lys Asp Thr Ile Leu Gln Leu Asn
            340                 345                 350
Leu Lys Glu Tyr Asn Leu Val
        355
```

<210> SEQ ID NO 14
<211> LENGTH: 5634
<212> TYPE: DNA
<213> ORGANISM: Mus musculus

<400> SEQUENCE: 14

```
gcgcggcggc cggctgcccg gtttgcgagc gagccgagtg ggcgcgggca ggccgagggc      60
gcccggagcc gagtcaggcg gcggcggcg cggcggcgag gagcgggcgc gccgggcgcg     120
ctgagccgtc ggcggtcgct cgctgcgggg ccgcctcggt ggatgagctc gggccgctgg     180
gcgcacagcc ttgggcagcg tcggcggcg cgcctggagg gccgcgcgct ctccgagaag     240
gcggcgtgtg agcgcggcgg ggcgcggcgg cctttcctcg cgcgtcccag gctcccggcc     300
ccgctcgttc ccggcccgcc tgggctgcgg gcccggccgc ctcctttacc gcggctcccc     360
tgagctcgtc cctgacgcgc gcccgggcgg cggggctccg cggccgccgc tgcctcgggg     420
gagcgagggc ggagggcgtg tgtgcgcgcg tgtgagcagg gcgccggcgg ggctgcagcg     480
aggcacttcg gaagaatgac tctggagtcc atcatggcgt gctgcctgag cgaggaggcc     540
aaggaagccc ggaggatcaa cgacgagatc gagcggcagc tgcgcaggga caagcgcgac     600
gcccgccggg agctcaagct gctgctgctg ggacagggg agagtggcaa gagcaccttc     660
atcaagcaga tgaggatcat ccacgggtcg ggctactctg acgaagacaa gcgcggcttc     720
accaagctgg tgtatcagaa catcttcacg gccatgcagg ccatgatcag agcgatggac     780
acgctcaaga tcccatacaa gtatgaacac aataaggctc atgcacaatt ggttcgagag     840
gttgatgtgg agaaggtgtc tgcttttgag aatccatatg tagatgcaat aaagagcttg     900
tggaatgatc ctggaatcca ggagtgctac gacagacgac gggaatatca gttatctgac     960
tctaccaaat actatctgaa tgacttggac cgtgtagccg acccttccta tctgcctaca    1020
caacaagacg tgcttagagt tcgagtcccc actacaggga tcatcgaata ccccttttgac    1080
```

-continued

```
ttacaaagtg tcattttcag aatggtcgat gtaggggggcc aaaggtcaga gagaagaaaa    1140
tggatacact gctttgaaaa tgtcacctcc atcatgtttc tagtagcgct tagcgaatat    1200
gatcaagttc ttgtggagtc agacaatgag aaccgcatgg aggagagcaa agcactcttt    1260
agaacaatta tcacctaccc ctggttccag aactcctctg tgattctgtt cttaaacaag    1320
aaagatcttc tagaggagaa atcatgtat tcccacctag tcgactactt cccagaatat    1380
gatggacccc agagagatgc ccaggcagct cgagaattca tcctgaaaat gttcgtggac    1440
ctgaaccccg acagtgacaa aatcatctac tcccacttca cgtgcgccac agataccgag    1500
aacatccgct tcgtctttgc agccgtcaag gacaccatcc tgcagctgaa cctgaaggag    1560
tacaatctgg tctaaccgtg cctcccagaa accgttcttc cctcccctgt gggttgttga    1620
agataaacaa gagggactgt atttctgtgg aaaacaattt gcataatact aatttattgc    1680
cgtcctggac tctgtgagcg tgtccacaga gctgtagtaa atattatgat tttatttaaa    1740
ctattcagag gaaacaggat gctgaagtac agtcccagca catttcctct tttttttttt    1800
ttaggcaaac cttgatgtat tttaaatttt cagtcattca ctcacagtat aaaagcactc    1860
ctgtcattcg tgttctctct ctctctctct ctctctctct ctctctctct ctctctctct    1920
ctctctctct cattcctttc cttcttcctc ctcccctttc cttttgacca aaacgaagct    1980
gatttttctt cttcctgctc cttccctccc tgctgatttt attctccctc actaccatgg    2040
ccttgccccc aatcccattc ttggccagtt tcccccaatc ccattcttgg gcagtttctc    2100
ccatcgagtg acgtagtcag gacggtgtta ttcgactgaa gccgccttac gtcagcttcc    2160
tttacccgtg gtctgctga aggcaggagc ataggtgttc gtactatggt tttaaatggt    2220
tctctggatg cacatcacat ctagcatttc tttttcaata catacataca tacatacata    2280
catatatatg tatactatat atattgtctt gtctcacttg cactaggaca gtgggtaccc    2340
attgatgatc aagagtcgta tcttttgggt gcagaccttc agccacagca ggattgttaa    2400
gagaaatgga tggaggtcag ggtgtgaggg cacaggctgg gaagaagtcc ttgcttctca    2460
aggccacgta ccggccgcgt ccttccaccc ttgcccttta aaccacagat gccaaatgat    2520
acgccaacag acactacatt ccccagcagc tgctgccaga gccctcttgt agcttcttta    2580
ttttctgttt ctttccagct ttcctaccct cctatcccc cttgtgtttg ggccacaatt    2640
ttgaaataat ttttattata ggtatgtgct gccaaagcca gattttttata aggtaaaata    2700 aattaagaat ttaaacagta aaagccagtg tctcaaaatg tcagcattaa aatgtgaagg    2760
ggacagcagg gtgtgaaccg gaaacacaca ttgccaaaca gttgccaact gaactgctgc    2820
ttctcatggt ccgttctttt ctttgcccctt aaggtcaatg ccagtgtcca gacgagcagt    2880
gtagaaaagc tccctgtgtg gtttgtcgtg aggtctgctt gtatctcttc actggcgtta    2940
gtttcattag ctctttattc tccttacgtt cgagtgaatc tgccaagaac actggtggat    3000
agtattatcc taacactttt ggtttggggg cggggagggg gcagggaata gtgagctggc    3060
tttaccacct tcaggatctc gaattgggcg cttgaaccta agaaagattg tggacttatc    3120
aaaagtcacc gctcagtgtt ccgtcaagca tgtatttatg tgacgatcat actaggaggg    3180
atgtttggaa ttctccatgt gcaatttgtc cgcagatgca aactgtgccg aacgtgtgtg    3240
agtgagcctg tcaagcagcc tgcatcagtg tgtgatttaa gtagatgcg agcgctctaa    3300 ggctgccggg aagtcagacc tcgatgctgg tctcattagc gcttggcact aatctcaact    3360
ccatagacat cactttcttt gaatagcaaa gctgggagag tgaccagctc actgtatgaa    3420
cacggacatt gctgactggt aatgaagtgc tctcatgtgt tactctcctg gctctttcat    3480
```

-continued

```
ccccttgctct agaaagcccc tgtaatttaa ttaacagact gcctgtaggt atagtgcaat    3540
tatgaatgct ctgatcgttg tacatacatc tctcttgata ttgcaacatc catactggct    3600
ttgtaatcat taattttttg gcagattgaa tgtgctgtat tgatatgtat ctatgtaatt    3660
gtatgtctta tagctaattc acattttgaa taatgttatt ttatttactt ttttaagaga    3720
ggagaatgta aatttgtcag tttatttctg actagggata ttttttttcca tttagaaaag    3780
aagaaaaaaa aaaaaaccct tactattgta cagagcggta ctagcatcgt gctgtctaaa    3840
atcatttgca cattcctgag tagaggtgtg ctgacctaag acccaaaggt aatttcatag    3900
caaacacaca ccatccgtca gagcttttat acaaacacgg agaccaactt tgtagacctt    3960
ttgccatttg acctggggtt ggaatatgag cttttatacg attcatattc ttatttggca    4020
aatgcacagt ttagcattac ctctctggtg gcctttatta gaaaggcagt tttagaagct    4080
atttgtgatc cactaaggaa atgttttatc agctagagac cactgcttgc ctgaaagggc    4140
aaccttaaat ttggtgcagc aaaaaacaaa aaacaaaaa aaacaaaaac aaaaacaaaa    4200
caaacaaaac aaaaaataaa aacaaaaaaa tttaaaaaca caaaaagaca aaaagaaga    4260
aaaaagtaac atttgatggc ctgcagtgta tagagaaaac ctcatcccag gatcataagt    4320
gttaaccgtc ctaaggaagc gagctgttct gtctaataga gctgtagtgg atggagctga    4380
gccgtgctga taccaagctc agagctgctg agtaaggcag ggagaggtgg ccacgttgtc    4440
tttatgaatt gagggtgcag cttgctgctg cacagagttg aagtctggcc tcactgcaca    4500
tcctgggggtg catgacagag tcccttcttc tgagaaggga aaacattgat caccctagct    4560
gcagtggtgc ctgcacacct tactctatcc acactagtca atgaagctaa aactaatttt    4620
gttgttgttt ctcgtttggg gttttattga aggggtgagg ggcgggaagg gcttcttagt    4680
tttgtacaaa aacaaagttt actcatatgc tttctcttct attgtgattg caagtgttcc    4740
tgttgtcgat gctctaggta atggaggctt gtgatgagcg ttatggtgac ttgggcatgt    4800
cttattcaga agcaaaacac agaccacaga aacctttcct cagcatacca aggcaagcag    4860
ccatctcatg agtcactcag cacatgagtg tgccgtttac agatgatgtc gccttttgt    4920
gtgtgatacg gcagttccca cccacagaga attcctattt gtaaattgga ggtttatact    4980
atgccttaca gagcttaaat tcagaagtct gtgcctcatg tctgaaacaa agggaaaaca    5040
cacgcccatg cagaagtcag ttaagtctta cagagcctgt tgggtttttcc ttatcgtttc    5100
cttaggaaga gctctgttga atgtcctgag tagctgggaa attcttctta ggagcctgcg    5160
tatattgttt actggcaggt ggcatccacg gcgatattta agaacaccct ggaacttggg    5220
ggcttggggg ctttgttttg ttttgttttt gtttagatta cattagcagg cctaatcatt    5280
ttaaagggta attcagccaa agggcaattt acttttttgta cttcagactt ctattgattg    5340
tcaagttgta cgaattgtaa tttaaaaatt tatactgcca catgattgta aatttttagtt    5400
gtcttaagta ggaattggtg aaaagctgtt tatgctggat ttgggtcaaa atgacttgat    5460
tatttgcaaa aaataaaact aataatggga agaaagggct gcataacaag acaccgcaag    5520
actcagattc cctcagatga cccccagcgcc cctttgttct cagtttctca aaagaacgaa    5580
tgaagtgaaa catagcagaa tgttaaccca tataaaataa agtgtaccca aata           5634
```

<210> SEQ ID NO 15
<211> LENGTH: 359
<212> TYPE: PRT
<213> ORGANISM: Rattus norvegicus

<400> SEQUENCE: 15

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Val Arg Ala Met Asp Thr
            85                  90                  95

Leu Lys Ile Pro Tyr Lys Tyr Glu His Asn Lys Ala His Ala Gln Leu
        100                 105                 110

Val Arg Glu Val Asp Val Glu Lys Val Ser Ala Phe Glu Asn Pro Tyr
    115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
            165                 170                 175

Gln Asp Val Leu Arg Val Arg Val Pro Thr Thr Gly Ile Ile Glu Tyr
        180                 185                 190

Pro Phe Asp Leu Gln Ser Val Ile Phe Arg Met Val Asp Val Gly Gly
    195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
            245                 250                 255

Thr Ile Ile Thr Tyr Pro Trp Phe Gln Asn Ser Ser Val Ile Leu Phe
        260                 265                 270

Leu Asn Lys Lys Asp Leu Leu Glu Glu Lys Ile Met Tyr Ser His Leu
    275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
            325                 330                 335

Ile Arg Phe Val Phe Ala Ala Val Lys Asp Thr Ile Leu Gln Leu Asn
        340                 345                 350

Leu Lys Glu Tyr Asn Leu Val
        355
```

<210> SEQ ID NO 16
<211> LENGTH: 1080
<212> TYPE: DNA
<213> ORGANISM: Rattus norvegicus -continued

<400> SEQUENCE: 16

```
atgactctgg agtccatcat ggcgtgctgc ctgagcgagg aggccaagga agcccggagg      60
atcaacgacg agatcgagcg gcagctgcgc agggacaagc gcgacgcccg ccgggagctc     120
aagctgctgc tgctggggac aggggagagt ggcaagagta ccttcattaa gcagatgagg     180
atcatccacg gtcggggta ctctgatgaa gacaagaggg gctttaccaa actggtgtat      240
cagaacatct ttacagccat gcaggccatg gtcagagcta tggacactct caagatccca     300
tacaagtatg aacacaataa ggctcatgca caattggttc gagaggttga tgtggagaag     360
gtgtctgctt ttgagaatcc atatgtagac gcaataaaga gcttgtggaa tgatcctgga     420
atccaggaat gctacgatag acggcgagaa tatcagctat ctgactctac caatactat      480
ctgaacgact tggaccgtgt ggctgacccct cctatctgc ctacacaaca agatgtgctt     540
agagttcgag tccccaccac agggatcatt gagtacccct tcgacttaca gagtgtcatc     600
ttcagaatgg tcgatgtagg aggccaaagg tcagagagaa gaaatggat acactgcttt      660
gaaaacgtca cctcgatcat gtttctggta gcgcttagcg aatacgatca agttcttgtg     720
gagtcagaca atgagaaccg aatggaggag agcaaagcac tctttagaac cattatcaca     780
tatccctggt tccagaactc ctctgttatt ctgttcttaa acaagaaaga tcttctagag     840
gagaaaatta tgtattccca cctagtcgac tacttcccag aatatgatgg accccagaga     900
gatgcccagg cagcacgaga attcatcctg aagatgttcg tggacctgaa ccccgacagt     960
gacaaaatca tctactcgca cttcacgtgt gccacagaca cggagaacat ccgcttcgtg    1020
tttgctgctg tcaaggacac catcctgcag ctgaacctga aggagtacaa tctggtctaa    1080
```

<210> SEQ ID NO 17
<211> LENGTH: 472
<212> TYPE: PRT
<213> ORGANISM: Homo sapiens

<400> SEQUENCE: 17

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
    130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175
```

```
Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
            195                 200                 205

Asp Gly Val Tyr Lys Val Phe Asn Gly Lys Asp Asn Ile Ser Lys Val
            210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                    245                 250                 255

Phe Val Glu Lys Ser Gln Val Leu Gln Phe Phe Ser Ser Asp Ile Cys
                260                 265                 270

Arg Ser Ile Tyr Ala Val Phe Glu Ser Asp Val Asn Leu Lys Gly Ile
            275                 280                 285

Pro Val Tyr Arg Phe Val Leu Pro Ser Lys Ala Phe Ala Ser Pro Val
            290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
                340                 345                 350

Val Ser Glu Pro Ile Asp Gly Leu Asn Pro Asn Glu Glu His Arg
            355                 360                 365

Thr Tyr Leu Asp Ile Glu Pro Ile Thr Gly Phe Thr Leu Gln Phe Ala
                370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
                420                 425                 430

Gln Val Thr Gly Lys Ile Asn Leu Gly Leu Ile Glu Met Ile Leu
                435                 440                 445

Leu Ser Val Gly Val Val Met Phe Val Ala Phe Met Ile Ser Tyr Cys
450                 455                 460

Ala Cys Arg Ser Lys Thr Ile Lys
465                 470

<210> SEQ ID NO 18
<211> LENGTH: 2069
<212> TYPE: DNA
<213> ORGANISM: Homo sapiens

<400> SEQUENCE: 18
gaggatgtca atggctttca gatgtcagga taaccttaag gatagatgaa gggttgagag    60
cctgtgcctc atttctgagt tctcagctgc tatgccgtgg aaatcctgtt tactttctgc   120
atctgctcct gcaagactct ggagccagtc ttgaggtcct acatctccga agcaagctc    180 ttctagaagt tgatagcttt ccaatgatta gacgaattga ttctttctgt gactcatcag   240
ttcatttcct gtaaaattca tgtcttgctg ttgatttgtg aataagaacc agagcttgta   300
gaaaccactt taatcatatc caggagtttg caagaaacag gtgcttaaca ctaattcacc   360
tcctgaacaa gaaaatgggc tgtgaccgg aactgtgggc tcatcgctgg ggctgtcatt   420
```

-continued

```
ggtgctgtcc tggctgtgtt tggaggtatt ctaatgccag ttggagacct gcttatccag    480
aagacaatta aaaagcaagt tgtcctcgaa gaaggtacaa ttgcttttaa aaattgggtt    540
aaaacaggca cagaagttta cagacagttt tggatctttg atgtgcaaaa tccacaggaa    600
gtgatgatga acagcagcaa cattcaagtt aagcaaagag tccttatac gtacagagtt     660 cgttttctag ccaaggaaaa tgtaacccag gacgctgagg acaacacagt ctctttcctg    720
cagcccaatg gtgccatctt cgaaccttca ctatcagttg aacagaggc tgacaacttc     780 acagttctca atctggctgt ggcagctgca tcccatatct atcaaaatca atttgttcaa    840
atgatcctca attcacttat taacaagtca aaatcttcta tgttccaagt cagaactttg    900
agagaactgt tatggggcta tagggatcca ttttttgagtt tggttccgta ccctgttact    960
accacagttg gtctgtttta tccttacaac aatactgcag atggagttta taagttttc    1020 aatggaaaag ataacataag taaagttgcc ataatcgaca catataaagg taaaaggaat   1080
ctgtcctatt gggaaagtca ctgcgacatg attaatggta cagatgcagc tcatttcca    1140 ccttttgttg agaaaagcca ggtattgcag ttcttttctt ctgatatttg caggtcaatc   1200
tatgctgtat ttgaatccga cgttaatctg aaaggaatcc ctgtgtatag atttgttctt   1260
ccatccaagg cctttgcctc tccagttgaa acccagaca actattgttt ctgcacagaa    1320
aaaattatct caaaaaattg tacatcatat ggtgtgctag acatcagcaa atgcaaagaa   1380
gggagacctg tgtacatttc acttcctcat tttctgtatg caagtcctga tgtttcagaa    1440
cctattgatg gattaaaccc aaatgaagaa gaacatagga catacttgga tattgaacct   1500
ataactggat tcactttaca atttgcaaaa cggctgcagg tcaacctatt ggtcaagcca   1560
tcagaaaaaa ttcaagtatt aaagaatctg aagaggaact atattgtgcc tattctttgg   1620
cttaatgaga ctgggaccat tggtgatgag aaggcaaaca tgttcagaag tcaagtaact   1680
ggaaaaataa acctccttgg cctgatgaaa atgatcttac tcagtgttgg tgtggtgatg   1740
tttgttgctt ttatgatttc atattgtgca tgcagatcga aaacaataaa ataagtaagt   1800
atgtaccaaa aaatattgct tcaataatat tagcttatat attacttgtt ttcactttat   1860
caaagagaag ttacatatta ggccatatat atttctagac atgtctagcc actgatcatt   1920
tttaaatata ggtaaataaa cctataaata ttatcacgca gatcactaaa gtatatctt    1980 aattctggga gaaatgagat aaaagatgta cttgtgacca ttgtaacaat agcacaaata   2040
aagcacttgt gccaaagttg tccaaaaaa                                     2069
```

<210> SEQ ID NO 19
<211> LENGTH: 472
<212> TYPE: PRT
<213> ORGANISM: Mus musculus

<400> SEQUENCE: 19

Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Met
            20                  25                  30

Leu Ile Gly Lys Thr Ile Lys Arg Glu Val Val Leu Glu Glu Gly Thr
        35                  40                  45

Thr Ala Phe Lys Asn Trp Val Lys Thr Gly Thr Thr Val Tyr Arg Gln
    50                  55                  60

Phe Trp Ile Phe Asp Val Gln Asn Pro Asp Asp Val Ala Lys Asn Ser
65                  70                  75                  80

```
Ser Lys Ile Lys Val Lys Gln Arg Gly Pro Tyr Thr Tyr Arg Val Arg
                85                  90                  95

Tyr Leu Ala Lys Glu Asn Ile Thr Gln Asp Pro Glu Asp His Thr Val
            100                 105                 110

Ser Phe Val Gln Pro Asn Gly Ala Ile Phe Glu Pro Ser Leu Ser Val
        115                 120                 125

Gly Thr Glu Asp Asp Asn Phe Thr Val Leu Asn Leu Ala Val Ala Ala
    130                 135                 140

Ala Pro His Ile Tyr Gln Asn Ser Phe Val Gln Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asp Thr Val
        195                 200                 205

Asp Gly Val Tyr Lys Val Phe Asn Gly Lys Asp Asn Ile Ser Lys Val
    210                 215                 220

Ala Ile Ile Glu Ser Tyr Lys Gly Lys Arg Asn Leu Ser Tyr Trp Pro
225                 230                 235                 240

Ser Tyr Cys Asp Met Ile Asn Gly Thr Asp Ala Ala Ser Phe Pro Pro
                245                 250                 255

Phe Val Glu Lys Ser Arg Thr Leu Arg Phe Phe Ser Ser Asp Ile Cys
            260                 265                 270

Arg Ser Ile Tyr Ala Val Phe Gly Ser Glu Ile Asp Leu Lys Gly Ile
        275                 280                 285

Pro Val Tyr Arg Phe Val Leu Pro Ala Asn Ala Phe Ala Ser Pro Leu
    290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                325                 330                 335

Lys Pro Val Tyr Ile Ser Leu Pro His Phe Leu His Ala Ser Pro Asp
            340                 345                 350

Val Ser Glu Pro Ile Glu Gly Leu His Pro Asn Glu Asp Glu His Arg
        355                 360                 365

Thr Tyr Leu Asp Val Glu Pro Ile Thr Gly Phe Thr Leu Gln Phe Ala
    370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
                405                 410                 415

Asn Glu Thr Gly Thr Ile Gly Asp Glu Lys Ala Glu Met Phe Lys Thr
            420                 425                 430

Gln Val Thr Gly Lys Ile Lys Leu Leu Gly Met Val Glu Met Ala Leu
        435                 440                 445

Leu Gly Ile Gly Val Val Met Phe Val Ala Phe Met Ile Ser Tyr Cys
    450                 455                 460

Ala Cys Lys Ser Lys Asn Gly Lys
465                 470
```

<210> SEQ ID NO 20
<211> LENGTH: 3016
<212> TYPE: DNA
<213> ORGANISM: Mus musculus

<400> SEQUENCE: 20

```
actgaggact ttttcttctt cacagctgcc ttctgaaatg tgtggagcaa ctggtggatg      60
gtttcctagc ctttcaaagg tagtttacaa atgatttgaa gtgctgatcc tttcagagtc     120
tcaacagatt atttcttaaa cagctcatac attgctgttt atgcatgaat tagtagaacc     180
gggccacgta gaaacactg tgattgtacc tgggagttgg cgagaaaacc agtgctctcc      240
cttgattctg ctgcacgagg agaatgggct gtgatcggaa ctgtgggctc attgctggag     300
ctgttattgg tgcagtcctg gctgtgtttg gaggcattct catgccagtc ggagacatgc     360
ttattgggaa gacaatcaaa agggaagttg tccttgaaga aggaaccact gctttcaaaa     420
actgggttaa aacaggcacc actgtgtaca gacagttttg gatctttgat gtgcaaaacc     480
cagatgacgt ggcaaagaac agcagcaaaa tcaaggttaa acaaagaggt ccttacacat     540
acagagttcg ttatctagcc aaggaaaata taactcagga ccccgaggac cacactgtgt     600
cttttgtaca gcccaatgga gccatctttg agccttcact gtctgttgga acagaggatg     660
acaacttcac agttctgaat ctggctgtag cagctgcacc acatatctac caaaattcat     720
tgttcaagt tgtgctcaac tctcttataa aaagtccaa gtcttctatg ttccaaacaa       780
gatctttgaa agaactcttg tggggttaca agatccatt cctcagtttg gttccatatc      840
ctataagtac cacagttggt gtgttttatc cttacaatga cactgtagat ggagtttata     900
aagttttcaa tggaaaggat aacataagca agttgccat aattgagtcc tataaaggga     960
aaaggaattt gtcctattgg ccaagctatt gcgacatgat taatggcaca gacgcagcct    1020
cctttccacc ttttgttgaa aagtctcgga cattgagatt cttttcctct gacatttgca    1080
ggtctatcta cgctgtgttc ggatctgaaa tcgaccttaa aggaatcccc gtgtacagat    1140
tgttcttcc agccaatgcc tttgcatcac ccctccagaa tccagacaac cattgtttct    1200
gcactgaaaa agtaatctcc aataactgta catcttatgg tgtgctagac attggcaaat    1260
gcaaagaagg aaagcctgtg tatatttcgc ttccacattt cctacatgca agtccagatg    1320
tttcagaacc tattgaaggc ttacatccaa atgaagatga gcataggaca tacttagatg    1380
tggaacccat aactggattc actctacaat ttgcaaaacg actgcaggtc aacatattgg    1440
tcaagccagc tagaaaaata gaagcattaa agaatctgaa gagaccttac attgtaccta    1500
tactgtggct aaatgagact gggaccattg gtgatgaaaa agcagaaatg ttcaaaacac    1560
aagtgactgg gaaaatcaag ctccttggca tggtagagat ggccttactt gggattggag    1620
tggtgatgtt tgttgctttt atgatttcat attgtgcttg caaatccaag aatggaaaat    1680
aagtagtgga tgagcctaca tatacactgg ctacatcttt ggtaaagccg atctacaaaa    1740
tgaaaactta atatatgctt cgttttaca aaacacacct atcttaggga gaagaaatgg    1800
tggtgtgtgc tctctctctc tttctctttc tctcttattg cagatatata tttatttgta    1860
aatatatata tatgcaataa gtcacagcat atttcaaaag attaatatgt cactataggc    1920
aatattttt aataaaatct gcactttta ttaaaagtcc atcatttgca actgagtgga     1980
cttcaattc tgtagaccca attatcctgt ttggttctga tttactgatt tgttccatgt    2040
tggcaaattt caagaatgta cattctgaga aatttttgtt ttccctcact ggaggaaact    2100
gctatcatga ctggggtggc cccttgtttt atagcaaatt tggcttgcaa ctgtcagcac    2160
```

-continued

```
atggcataag tataacatct tgaaagactt aagaatgaaa atgaacaat  tcacatgtga   2220
gccactgctt atatattaag tctctccctc tctggagttc ttggctacag caaggccaga   2280
tatcacattg gttttggttt tgttgttttt gttttgtttt tgtttttac  tctctgacac   2340
agagcttatg aaatggactt ttttttttt ttttagcata ccttagctct ttgtatttta   2400
agtatgtcgt catgttccat gctgcatagc tctttaaaaa acctgagtag gttttctct    2460
ttctgctcag ctgcaactaa taacaacctt ggagagctgt tatagtgtta aaagatgtaa   2520
atgataataa aagaattatt aaatggaatc ctacaaaagc aacaatgggc tttaatatat   2580
atttgtggta atatctcctg ctttcataat  cacccaaaaa aaggactggt ttctaacatt   2640
aaaagaagtc gttccttaaa ttcaacctt  ttgtctagtt actattgaat cacagtatgt   2700
tatttattgt attttatttt gttttttgta gaagtgttct atctgagatt ctgtgtcctt   2760
ctgaatcatt taacctttct gctatgtctt aatgcaattg aacacagata ttttgttata   2820
attttatagc agcagtgtga gactgaaggc aaatattttc cagggtaaga cacagtgata   2880
ggttgttcta cttcctttag cagcataatc aatttcactt agtattagtc ccaataaatt   2940
ctggtataag acacaaaata aaaacaaaca ttttctgttc tatacgtaga aaataaaag    3000
gaaaggtgag acaact                                                   3016
```

<210> SEQ ID NO 21
<211> LENGTH: 472
<212> TYPE: PRT
<213> ORGANISM: Rattus norvegicus

<400> SEQUENCE: 21

```
Met Gly Cys Asp Arg Asn Cys Gly Leu Ile Thr Gly Ala Val Ile Gly
1               5                   10                  15

Ala Val Leu Ala Val Phe Gly Gly Ile Leu Met Pro Val Gly Asp Leu
            20                  25                  30

Leu Ile Glu Lys Thr Ile Lys Arg Glu Val Val Leu Glu Glu Gly Thr
        35                  40                  45

Ile Ala Phe Lys Asn Trp Val Lys Thr Gly Thr Thr Val Tyr Arg Gln
    50                  55                  60

Phe Trp Ile Phe Asp Val Gln Asn Pro Glu Glu Val Ala Lys Asn Ser
65                  70                  75                  80

Ser Lys Ile Lys Val Lys Gln Arg Gly Pro Tyr Thr Tyr Arg Val Arg
                85                  90                  95

Tyr Leu Ala Lys Glu Asn Ile Thr Gln Asp Pro Lys Asp Ser Thr Val
            100                 105                 110

Ser Phe Val Gln Pro Asn Gly Ala Ile Phe Glu Pro Ser Leu Ser Val
        115                 120                 125

Gly Thr Glu Asn Asp Asn Phe Thr Val Leu Asn Leu Ala Val Ala Ala
    130                 135                 140

Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asn Thr Val
        195                 200                 205

Asp Gly Val Tyr Lys Val Phe Asn Gly Lys Asp Asn Ile Ser Lys Val
    210                 215                 220
```

```
Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
            245                 250                 255

Phe Val Glu Lys Ser Arg Thr Leu Arg Phe Phe Ser Ser Asp Ile Cys
        260                 265                 270

Arg Ser Ile Tyr Ala Val Phe Gly Ser Glu Val Asn Leu Lys Gly Ile
    275                 280                 285

Pro Val Tyr Arg Phe Val Leu Pro Ala Asn Ala Phe Ala Ser Pro Leu
290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
            325                 330                 335

Lys Pro Val Tyr Ile Ser Leu Pro His Phe Leu His Ala Ser Pro Asp
        340                 345                 350

Val Ser Glu Pro Ile Glu Gly Leu Asn Pro Asn Glu Asp Glu His Arg
    355                 360                 365

Thr Tyr Leu Asp Val Glu Pro Ile Thr Gly Phe Thr Leu Gln Phe Ala
370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
            405                 410                 415

Asn Glu Thr Gly Thr Ile Gly Asp Glu Lys Ala Glu Met Phe Arg Asn
        420                 425                 430

Gln Val Thr Gly Lys Ile Lys Leu Leu Gly Leu Val Glu Met Val Leu
    435                 440                 445

Leu Gly Val Gly Val Val Met Phe Val Ala Phe Met Ile Ser Tyr Cys
450                 455                 460

Ala Cys Arg Ser Lys Asn Gly Lys
465                 470

<210> SEQ ID NO 22
<211> LENGTH: 2625
<212> TYPE: DNA
<213> ORGANISM: Rattus norvegicus

<400> SEQUENCE: 22
tggacttgta ctctctcctc ggatggctag ctgattactt ctgtgtagta gcttacaaat      60
gattcgaagt gttgaaactt tctgagtctc aatgaactat ttctcacaca actcagatac     120
tgctgttcat gcatgaatta gttgaaccag gccacataga aagcattgta attgtacctg     180
tgagttggca agaagcaagt gctcttcctt gattctgctg cacgaggagg agaatgggct     240
gcgatcggaa ctgtgggctc attactggag ccgttattgg tgctgtcctg gctgtgtttg     300
gaggcattct catgccggtt ggagacctac tcattgagaa acaatcaaa agggaagttg      360 tccttgaaga aggaaccatt gctttcaaaa actgggtgaa acgggcacc actgtgtaca      420 gacagttttg gatctttgac gtgcaaaacc cagaggaagt ggcaaagaat agcagcaaga     480
tcaaggttaa acagagaggt ccttacacat acagagttcg ttatttagcc aaggaaaata     540
taactcagga ccccaaggac agcactgtct cttttgtaca acccaatgga gccatctttg     600
agccttcact gtctgttgga acagagaatg acaacttcac agttctcaat ctggctgtgg     660
cagctgcacc acatatctac acaaaactcat ttgttcaagg tgtgctcaac agccttatca    720
```

```
aaaagtccaa gtcttctatg ttccaaacac gaagtttgaa ggaactcttg tggggttaca      780
aagatccatt cttgagtttg gttccatatc ctataagtac cacagttggt gtgttttatc      840
cttacaataa cactgtagat ggagtttata aagttttcaa tggaaaggat aacataagca      900
aggttgccat aattgatacc tataaaggga aaaggaattt gtcctattgg gaaagttatt      960
gcgacatgat taatggcaca gatgcagcct cctttccacc ttttgttgag aagtctcgaa     1020
cactgaggtt cttttcctct gacatttgca ggtccatcta tgctgtgttt ggatctgaag     1080
tgaaccttaa aggaatcccc gtgtacagat ttgttcttcc agccaacgcc tttgcctccc     1140
cactccagaa cccagacaac cactgtttct gcactgaaaa agtaatctca aataactgta     1200
cgtcgtatgg tgtgctggac attggcaagt gcaagaagg aaagcctgtg tacatttctc      1260
ttccacattt cctacatgca agtcctgatg tctcagaacc tatcgaaggc ttgaatccta     1320
acgaagatga gcataggaca tacttggatg tggaacccat aactggattc actctacagt     1380
ttgcaaaacg actgcaggtc aacatactgg tcaagccagc tagaaaaata gaagcactga     1440
agaatctgaa gagaccttac attgtaccta tactgtggct aaatgagact gggaccatcg     1500
gcgatgagaa agcagaaatg ttcagaaacc aagtgaccgg gaaaataaag ctcctgggcc     1560
tggttgagat ggtcttactt ggtgttggag tagtgatgtt tgttgctttt atgatttcat     1620
actgtgcttg cagatctaag aatggaaaat aagtagtgga tgagcctaca ttatgcacta     1680
gctacatttt tggtaaaacc aatctccaaa acgaagactt aagacatgct tgtttttata     1740
aaacacacct atctgtagtt gaagaaacgg tggtgtgcgc gctctctctc ttattgcaga     1800
tatatattta tttatatatt gcaataagcc acagcatatt tcgaaaagat taatatgtca     1860
ctaagcctat attttttaat aaaatcttgt attttgttaa gtccatcatc tgcaactgag     1920
tggacatcaa tttctgcaga actaattatc tttttggtt ctgatttact gatttttttt      1980
cctgttggca aatttcaaga atgtatatat tctaagaaac gctttgttcc tcatcgaagt     2040
aaactgttat catgtctggg gtggcccttt catttatagc aaatgttcct tgtgactgtc     2100
agcacatgat atgtcataag gattatatca ttttaaagat ttaaggatga aaaatgaaca     2160
attcacatat gaaccattgt tgatatattg tttaatcctc tccctctctg gtgtccttgg     2220
caacaacaag gccaggtatc acagatactt ttttctttt actttcttac acagagctta      2280
tatgttctgt tcctcgccat gaaatgaact atttttagca catttagct ctttatttta      2340
agtatgttgt caagttccat gctgcctagc tctttgaaa actgagtagg tttttctctt      2400
tctgctcagc cgcaactaat gtaacttcag agagctgtta tagtgttaaa agatgtaatt     2460
tataataaat ggattatgat atagaatctt aaaaagcta gaattggctt taaatatgta      2520
tttgtggtaa tatattctgc ttttataatc acccagaaat aactggtttc taacattaaa     2580
gatgttctta aattcaaaaa aaaaaaaaaa aaaaaaaaa aaaaa                      2625
```

NUCLEIC ACID MOLECULES ENCODING GPR84

BACKGROUND OF THE INVENTION

Taste signaling is found throughout the animal kingdom, from simple metazoans to the most complex of vertebrates. Taste sensation is believed to be mediated by receptors, i.e., metabotropic or inotropic receptors. Cells which express taste receptors, when exposed to certain chemical stimuli, elicit taste sensation by depolarizing to generate an action potential, which triggers the sensation. As such, taste receptors specifically recognize molecules that elicit specific taste sensation. These molecules are also referred to herein as "tastants." Many taste receptors belong to the 7-transmembrane receptor superfamily (Hoon, et al. (1999) *Cell* 96:451; Adler, et al. (2000) *Cell* 100:693), which are also known as G protein-coupled receptors (GPCRs). Other tastes are believed to be mediated by channel proteins.

The biochemical analysis and molecular cloning of a number of such receptors has revealed basic principles regarding the function of these receptors. For example, U.S. Pat. No. 5,691,188 describes how upon a ligand binding to a GPCR, the receptor presumably undergoes a conformational change leading to activation of the G protein. G proteins are comprised of three subunits: a guanyl nucleotide binding $\alpha$ subunit, a $\beta$ subunit, and a $\gamma$ subunit. When GDP is bound, the G protein exists as a heterotrimer, the G$\alpha\beta\gamma$ complex. When GTP is bound, the $\alpha$ subunit dissociates from the heterotrimer, leaving a G$\beta\gamma$ complex. When a G$\alpha\beta\gamma$ complex operatively associates with an activated G protein-coupled receptor in a cell membrane, the rate of exchange of GTP for bound GDP is increased and the rate of dissociation of the bound G$\alpha$ subunit from the G$\alpha\beta\gamma$ complex increases. The free G$\alpha$ subunit and G$\beta\gamma$ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell.

Mammals are believed to have five basic taste modalities, sweet, bitter, sour, salty, and umami (the taste of monosodium glutamate). See, e.g., Kinnamon, et al. (1992) *Ann. Rev. Physiol.* 54:715-31; Lindemann (1996) *Physiol. Rev.* 76:718-66; Stewart, et al. (1997) *Am. J Physiol.* 272:1-26. Numerous physiological studies in animals have shown that taste receptor cells may selectively respond to different chemical stimuli. See, e.g., Akabas, et al. (1988) *Science* 242:1047-50; Gilbertson, et al. (1992) *J. Gen. Physiol.* 100:803-24; Bernhardt, et al. (1996) *J. Physiol.* 490:325-36; Cummings, et al. (1996) *J. Neurophysiol.* 75:1256-63.

Much is known about the psychophysics and physiology of taste cell function. Thus, the identification and isolation of novel taste receptors and taste signaling molecules could allow for new methods of chemical and genetic modulation of taste transduction pathways. For example, the availability of receptor and channel molecules permits the screening for high affinity agonists, antagonists, inverse agonists, and modulators of taste activity. Such taste modulating compounds could be useful in the pharmaceutical and food industries to improve the taste of a variety of consumer products, or to block undesirable tastes, e.g., in certain pharmaceuticals.

Complete or partial sequences of various human and other eukaryotic chemosensory receptors are known. See, e.g., Pilpel & Lancet (1999) *Protein Science* 8:969-977; Mombaerts (1999) *Annu. Rev. Neurosci.* 22:487-50; Wang, et al. (2006) *J. Biol. Chem.* M608019200. See also, U.S. Pat. No. 5,874,243, WO 92/17585, WO 95/18140, WO 97/17444, WO 99/67282, and WO 2007/027661. In addition, the identification of ligands for G protein coupled receptors such as GPR84 has been conducted. See Wang, et al. (2006) supra; WO 2007/027661; and U.S. Patent Application No. 2007/0196867.

SUMMARY OF THE INVENTION

The present invention is an isolated nucleic acid molecule encoding CD36, G$_{qi9}$, and G protein-coupled receptor 84 (GPR84) proteins. Expression vectors with inducible or constitutive expression of CD36, G$_{qi}$9, and GPR84 are also embraced by the present invention, as is an isolated recombinant host cell which co-expresses CD36, G$_{qi9}$, and GPR84 proteins.

The present invention is also a method for identifying a modulator of GPR84 activity. The method involves contacting a recombinant host cell, which co-expresses CD36, G$_{qi9}$, and GPR84 proteins, with a test compound and determining the functional effect of the test compound on GPR84 activity thereby identifying a modulator of GPR84.

DETAILED DESCRIPTION OF THE INVENTION

The present invention provides isolated nucleic acid molecules encoding G protein-coupled receptor 84 (GPR84), CD36 and G$_{qi}$9, and use of the same in the identification of ligands for GPR84, e.g., agonists and antagonists. In particular, the present invention relates to GPR84 as a fat taste receptor and use of the same in screening assays for compounds that mimic fat taste.

As used herein, the term "isolated," when referring to a nucleic acid molecule refers to a state of purification or concentration different than that which occurs naturally. The nucleic acid molecules described herein may be isolated or otherwise associated with structures or compounds to which they are not normally associated in nature, according to a variety of methods and processed known to those of skill in the art.

GPR84 has been identified as a receptor for medium-chain free fatty acids (Wang, et al. (2006) supra). The GPR84 protein is found in a variety of species including human, mouse, rat, and the like and nucleic molecules encoding any one of these proteins can be used in accordance with the present invention. In this regard, the present invention embraces nucleic acid molecules encoding GPR84 proteins listed in Table 1.

TABLE 1

| Source | GENBANK Accession No. of Amino Acid Sequence | SEQ ID NO: | GENBANK Accession No. of Nucleic Acid Sequence | SEQ ID NO: | % Identity* |
|---|---|---|---|---|---|
| *Homo sapiens* | NP_065103 | 1 | NM_020370 | 2 | 100% |
| *Mus musculus* | NP_109645 | 3 | NM_030720 | 4 | 85.4% |
| *Rattus norvegicus* | NP_001102979 | 5 | NM_001109509 | 6 | 83.8% |
| *Bos taurus* | NP_001033657 | 7 | NM_001038568 | 8 | 89.6% |

*% Identity based on alignment with human GPR84 protein.

In some embodiments, the nucleic acid molecule encodes a human GPR84 protein. In other embodiments, the nucleic acid molecule encodes a human GPR84 protein of SEQ ID NO:1. In particular embodiments, the nucleic acid molecule encoding human GRP84 protein is set forth in SEQ ID NO:9.

Functionally, the GPR84 proteins disclosed herein are members of a family of related seven transmembrane G protein-coupled receptors, which are believed to be involved in taste transduction. Structurally, the nucleotide sequences of the GPR84 family members can encode related proteins including an extracellular domain, seven transmembrane domains, and a cytoplasmic domain. Related GPR84 family members from other species share at least about 60%, 70%, 80%, or 90% protein sequence identity over a region of at least about 50 amino acid residues in length, optionally 100, 200, 300, or more amino acid residues in length to SEQ ID NOs: 1, 3, 5 or 7.

Specific regions of the GPR84 amino acid sequences can be used to identify polymorphic variants, interspecies homologs, and alleles of GPR84 family members. This identification can be made in vitro, e.g., under stringent hybridization conditions or PCR (e.g., using primers encoding GPR84 consensus sequences), or by using the sequence information in a computer system for comparison with other nucleotide sequences. Different alleles of GPR84 genes within a single species population will also be useful in determining whether differences in allelic sequences correlate to differences in taste perception between members of the population. Classical PCR-type amplification and cloning techniques are useful for isolating orthologs, for example, where degenerate primers are sufficient for detecting related genes across species, which typically have a higher level of relative identity than paralogous members of the GPR84 family within a single species.

Typically, identification of polymorphic variants and alleles of GPR84 family members can be made by comparing an amino acid sequence of about 25 amino acids or more, e.g., 50-100 amino acids. Amino acid identity of approximately at least 60%, 70%, 75%, 80%, 85%, 90%, 95-99%, or above typically demonstrates that a protein is a polymorphic variant, interspecies homolog, or allele of a T1R family member. Sequence comparison can be performed using any conventional sequence comparison algorithms. Antibodies that bind specifically to GPR84 polypeptides or a conserved region thereof can also be used to identify alleles, interspecies homologs, and polymorphic variants.

In addition to GRP84, the nucleic acid molecule of the invention further encodes a chimeric guanine nucleotide-binding protein (G protein) composed of the G protein $\alpha_q$ subunit, wherein the C-terminal nine residues have been replaced by those of the G protein $\alpha_i$ subunit. This chimeric G protein, termed $G_{qi9}$, is known in the art and described by Parmentier, et al. (1998) *Mol. Pharmacol.* 53(4):778-86; Perroy, et al. ((2001) *J. Biol. Chem.* 276: 45800-45805) for coupling receptors to phospholipase C. By way of illustration, the nine C-terminal amino acid residues of the $G_q$ subunit set forth in GENBANK Accession No. NP_002063.2 (SEQ ID NO:10) are replaced with the nine C-terminal amino acid residues of the G protein $\alpha_i$ subunit, i.e., Asn-Asn-Leu-Lys-Asp-Cys-Gly-Leu-Phe (SEQ ID NO:11). While the human $G_q$ subunit is desirably employed in the present invention, non-human $G_q$ subunit can also be used. For example, the $G_q$ subunits listed in Table 2 would be suitable for use in the present invention.

TABLE 2

| Source | GENBANK Accession No. of Amino Acid Sequence | SEQ ID NO: | GENBANK Accession No. of Nucleic Acid Sequence | SEQ ID NO: | % Identity* |
|---|---|---|---|---|---|
| Homo sapiens | NP_002063 | 10 | NM_002072 | 12 | 100% |
| Mus musculus | NP_032165 | 13 | NM_008139 | 14 | 99.7% |
| Rattus norvegicus | NP_112298 | 15 | NM_031036 | 16 | 99.4% |

*% Identity based on alignment with human $G_q$ protein subunit.

$G_q$ subunits of use in accordance with the present invention desirably share at least about 90% protein sequence identity over a region of at least about 50 amino acid residues in length, optionally 100, 200, 300, or more amino acid residues in length to SEQ ID NOs: 10, 13, or 15. As described for GPR84, related sequences can be identified using a variety of conventional methods, using stringent hybridization conditions or antibody cross-reactivity.

Further included in the nucleic acid molecule of the present invention are sequences encoding CD36. It has been suggested that GPR120 and CD36 form an independent pathway for fatty acid reception (Matsumura, et al. (2007) *Biomed. Res.* 28:49-55). Moreover, it is contemplated that CD36 also functions in conjunction with GPR84 in fatty acid transport and sensing of dietary lipids. Thus, the present invention embraces the co-expression of CD36 with GPR84 and $G_{qi9}$. While the human CD36 is desirably employed in the present invention, non-human CD36 can also be used. For example, the CD36 proteins listed in Table 3 would be suitable for use in the present invention.

TABLE 3

| Source | GENBANK Accession No. of Amino Acid Sequence | SEQ ID NO: | GENBANK Accession No. of Nucleic Acid Sequence | SEQ ID NO: | % Identity* |
|---|---|---|---|---|---|
| Homo sapiens | NP_001001547 | 17 | NM_001001547 | 18 | 100% |
| Mus musculus | NP_031669 | 19 | NM_007643 | 20 | 86.4% |
| Rattus norvegicus | NP_113749 | 21 | NM_031561 | 22 | 87.9% |

*% Identity based on alignment with human CD36 protein.

In so far as the CD36 proteins disclosed herein function as fatty acid transporters, the present invention embraces other CD36 proteins sharing at least about 90% protein sequence identity over a region of at least about 50 amino acid residues in length, optionally 100, 200, 300, or more amino acid residues in length to SEQ ID NOs: 17, 19, or 21.

The amino acid sequences of the proteins of the invention can be identified by putative translation of the coding nucleic acid sequences. These various amino acid sequences and the coding nucleic acid sequences can be compared to one another or to other sequences according to a number of methods.

For example, in sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions, e.g., from 20 to 600, usually about 50 to about 200 or about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman ((1981) *Adv. Appl. Math.* 2:482), by the homology alignment algorithm of Needleman & Wunsch ((1970) *J. Mol. Biol.* 48:443), by the search for similarity method of Pearson & Lipman ((1988) *Proc. Natl. Acad Sci. USA* 85:2444), by computerized implementations of these algorithms (GAP, BESTFIT, FASTA, and TFASTA in the Wisconsin Genetics Software Package, Genetics Computer Group, Madison, Wis.), or by manual alignment and visual inspection (see, e.g., *Current Protocols in Molecular Biology* (1995) Ausubel, et al., eds. supplement).

A preferred example of an algorithm that is suitable for determining percent sequence identity are the BLAST and BLAST 2.0 algorithms, which are described by Latched, et al. (1977) *Nuc. Acids Res.* 25:3389-3402, and Altschul, et al. (1990) *J. Mol Biol.* 2 15:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al. (1990) supra; Altschul et al. (1977) *Nuc. Acids Res.* 25:3389-3402). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=4 and a comparison of both strands. For amino acid sequences, the BLASTP program uses as defaults a wordlength of 3, and expectation (E) of 10 and the BLOSUM62 scoring matrix (see, Henikoff & Henikoff (1989) *Proc. Nati. Acad. Sci. USA* 89:10915) alignments (B) of 50, expectation (E) of 10, M=5, Nz=4, and a comparison of both strands.

Another example of a useful algorithm is PILEUP. PILEUP creates a multiple sequence alignment from a group of related sequences using progressive, pairwise alignments to show relationship and percent sequence identity. It also plots a so-called "tree" or "dendogram" showing the clustering relationships used to create the alignment. PILEUP uses a simplification of the progressive alignment method of Feng & Doolittle ((1987) *J. Mol. Evol.* 35:351-360). The method used is similar to the method described by Higgins & Sharp ((1989) *CABIOS* 5:151-153). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package (Devereaux, et al. (1984) *Nuc. Acids Res.* 12:387-395).

As shown herein, comparison of the human protein sequences of the invention to all known proteins in the public sequence databases using BLASTP algorithm revealed strong homology to other GPR84, $G_q$ subunits and CD36 proteins having at least about 80% amino acid identity the human sequences.

As an alternative to direct amino acid or nucleic acid sequence comparisons, suitable GPR84, $G_q$ subunit and CD36 proteins can be identified by hybridization of nucleic acid molecules (e.g., the nucleic acid molecules disclosed in Tables 1-3, or probes thereof) under stringent hybridization conditions to nucleic acids from other species (e.g., genomic or cDNA sequences). The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen (1993) Techniques in Biochemistry and Molecular Biology, Hybridization with Nucleic Probes, "Overview of principles of hybridization and the strategy of nucleic acid assays". Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For selective or specific hybridization, a positive signal is at least two times background, optionally 10 times background hybridization. Exemplary stringent hybridization conditions can be as follows: 50% formamide, 5×SSC, and 1% SDS with incubation at 42° C. (or 5×SSC, 1% SDS with incubation at 65° C.) with a wash in 0.2×SSC and 0.1% SDS at 65° C. Such hybridizations and wash steps can be carried out for, e.g., 1, 2, 5, 10, 15, 30, 60, or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

As is clear from the present disclosure, the nucleic acid molecules encoding the GPR84, $G_q$ subunit and CD36 proteins of the invention can be isolated from a variety of sources, genetically engineered, amplified, synthesized, and/or expressed recombinantly according to methods well-known in the art. Isolation and expression of the proteins of the present invention can be performed as described below. PCR primers can be used for the amplification of nucleic acids encoding GPR84, $G_q$ subunit and CD36 proteins, and libraries of these nucleic acids can optionally be generated and screened for the identification of a suitable nucleic acid molecule for protein expression. Amplification methods are well-known in the art, and include, e.g., polymerase chain reaction, PCR (*PCR Protocols, a Guide to Methods and Applications* (1990) ed. Innis. Academic Press, NY, and *PCR Strategies* (1995) ed. Innis, Academic Press, Inc., NY); ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) *Proc. Natl. Acad. Sci. USA* 86:1173); self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491); automated Q-beta replicase amplification assay (see, e.g., Burg (1996) *Mol. Cell. Probes* 10:257-271) and other RNA polymerase-mediated techniques (e.g., NASBA; Cangene, Mississauga, Ontario). Primers can be designed to retain the original sequence of the protein of interest. Alternatively, the primers can encode amino acid residues that are conservative substitutions (e.g., hydrophobic for hydrophobic residue or functionally benign substitutions (e.g., do not prevent plasma membrane insertion, cause cleavage by peptidase, cause abnormal folding of receptor, and the like). Once amplified, the nucleic acids, either individually or as libraries, can be cloned according to methods known in the art. Indeed, techniques for the manipulation of nucleic acids, such as, for example, for generating mutations in sequences, subcloning, labeling probes, sequencing, hybridization and the like are well-described in the scientific and patent literature. See, e.g., Sambrook, ed. (1989) *Molecular Cloning: a Laboratory Manual* (2nd ed.), Vols. 1-3, Cold Spring Harbor Laboratory, and *Current Protocols in Molecular Biology* (1997) Ausubel, ed. John Wiley & Sons, Inc., New York.

As an alternative to amplification and/or cloning, nucleic acids of the invention can be synthesized in vitro by well-known chemical synthesis techniques, as described in, e.g., Carruthers (1982) *Cold Spring Harbor Symp. Quant. Biol.* 47:411-418; Adams (1983) *Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109. Double-stranded DNA fragments can then be obtained either by synthesizing the complementary strand and annealing the strands together under appropriate conditions, or by adding the complementary strand using DNA polymerase with an appropriate primer sequence.

Once obtained, nucleic acids encoding the GPR84, $G_q$ subunit and CD36 proteins are introduced into an expression vector for recombinant protein expression. Depending on the intended use (e.g., in phenotypic or ligand binding assays), any expression vector system can be used, including, in addition to mammalian cells, e.g., bacterial, yeast, insect, or plant systems. As used herein, the term "expression vector" refers to any recombinant expression system for the purpose of expressing a nucleic acid molecule of the invention, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

To achieve recombinant protein expression, it is desirable that the nucleic acids of the invention are operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant nucleic acid molecules and vectors, a promoter can be operably-linked to one or more nucleic acid molecules of the invention to direct expression of the desired nucleic acid in all or a subset of cells or tissues. A "promoter" is defined as an array of nucleic acids that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. In particular embodiments, constitutive or inducible promoters are employed. A "constitutive" promoter is a promoter that is active under most environmental and developmental conditions. Examples of constitutive promoters include, but are not limited to, the P-actin promoter and the CMV promoter. An "inducible" promoter is a promoter that is active under environmental or developmental regulation. Examples of inducible promoters include, but are not limited to, the human c-fos promoter, steroid-inducible promoters such as a glucocorticoid-inducible promoter, and small molecule inducible promoters such as the tetracycline regulated promoter. Promoters of the invention are The term "operably-linked" refers to a functional linkage between a nucleic acid expression control sequence (such as a promoter, or array of transcription factor binding sites) and a second nucleic acid molecule, wherein the expression control sequence directs transcription of the nucleic acid corresponding to the second sequence.

In accordance with some embodiments of the present invention, the nucleic acid molecules encoding GPR84, CD36 and $G_{qi9}$ are introduced, in tandem, into one expression vector for expression as individual proteins in a host cell. In other embodiments, the nucleic acid molecules encoding GPR84, CD36 and $G_{qi9}$ are each introduced into different expression vectors for co-expression in a host cell. In yet other embodiments, two expression vectors are employed with various combinations of nucleic acid molecules encoding GPR84, CD36 and $G_{qi9}$ (e.g., one expression vector harbors GPR84 and $G_{qi9}$ nucleic acids and the other expression vector harbors CD36 nucleic acids). In addition, it is further contemplated that the proteins of the present invention can be expressed as fusion proteins, e.g., a GPR84-$G_{qi9}$ fusion protein.

Wherein the nucleic acid molecules encoding GPR84, CD36 and $G_{qi9}$ are introduced, in tandem, into one expression vector for co-expression of individual proteins in a host cell, some embodiments embrace the use of one promoter for regulating the expression of all three proteins. In this regard, it is contemplated that the nucleic acid molecules encoding GPR84, CD36 and $G_{qi9}$ are separated from each other by Internal Ribosome Entry Sites (IRESs). IRES elements are known from viral and mammalian genes (Martinez-Salas (1999) Curr. Opin. Biotechnol. 10:458-64), and have also been identified in screens of small synthetic oligonucleotides (Venkatesan & Dasgupta (2001) Mol. Cell. Biol. 21:2826-37.). The IRES from the encephalomyocarditis virus has been analyzed in detail (Mizuguchi, et al. (2000) Mol. Ther. 1:376-82). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas (1999) supra).

Alternatively, other embodiments embrace tandem introduction of nucleic acid molecules encoding GPR84, CD36 and $G_{qi9}$ into one expression vector, wherein the coding sequence for each protein has its own regulatory sequences.

In this regard, specific embodiments of the invention include a nucleic acid molecule containing, in order, the following sequences: promoter[1]→CD36 coding sequence→polyA signal→promoter[2]→$G_{qi9}$ coding sequence→polyA signal→promoter[3]→GPR84 coding sequence→polyA signal, wherein promoter[1-3] can be the same or different, or inducible or constitutive.

Expression vectors, either as individual expression vectors for co-expressing GPR84, CD36 or $G_{qi9}$ proteins, or one expression vector harboring nucleic acids encoding GPR84, CD36 and $G_{qi9}$ proteins can be introduced into a genome or into the cytoplasm or a nucleus of a host cell and expressed by a variety of conventional techniques well-described in the scientific and patent literature. See, e.g., Roberts, (1987) Nature 328:731; and Sambrook, ed. (1989) supra). Product information from manufacturers of biological reagents and experimental equipment also provide information regarding known biological methods. The vectors can be isolated from natural sources, obtained from such sources as ATCC or GENBANK libraries, or prepared by synthetic or recombinant methods.

The nucleic acids of the invention can be expressed in expression cassettes or vectors (including plasmids and viruses) which are stably or transiently maintained in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron) to permit selection of those cells transformed with the desired DNA sequences (see, e.g., Blondelet-Rouault (1997) Gene 190:315-317; Aubrecht (1997) J. Pharmacol. Exp. Ther. 281:992-997).

Also within the scope of the invention are recombinant host cells for co-expressing the proteins of the invention. Proteins of the invention are said to be "co-expressed" in that the host cell, when transformed with nucleic acids encoding GPR84, CD36 or $G_{qi9}$ proteins, transcribes and translates GPR84, CD36 or $G_{qi9}$ proteins. By "host cell" is meant a cell that contains an expression vector and supports the replication or expression of the expression vector. Host cells can be prokaryotic cells such as E. coli, or eukaryotic cells such as yeast, insect, amphibian, or mammalian cells such as CHO, HeLa, HEK-293, and the like, e.g., cultured cells, explants, and cells in vivo.

As indicated, the host cell can be mammalian or non-mammalian, with preference given to mammalian host cells. Any of the well-known procedures for introducing the expression vector(s) of the invention into host cells can be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA or other foreign genetic material into a host cell (see, e.g., Sambrook et al. supra) After the expression vector is introduced into the host cells, the transfected cells are cultured under conditions favoring expression of the proteins of the invention. Host cells of the invention which co-express GPR84, CD36 or $G_{qi9}$ proteins from one or more expression vectors find application in analyzing fatty acid transport and sensing of dietary lipids as well as in methods for identifying agents which modulate GPR84 activity.

Accordingly, the invention also provides methods of screening for modulators, e.g., activators, inhibitors, stimulators, enhancers, agonists, and antagonists, of GPR84 activity. Such modulators of GPR84 activity are useful for pharmacological, chemical, and genetic modulation of taste signaling pathways. These methods of screening can be used to identify high affinity agonists and antagonists of taste cell activity. These modulatory compounds can then be used in the food and pharmaceutical industries to customize taste, e.g., to modulate the tastes of foods.

"Inhibitors," "activators," and "modulators" of GPR84 activity are used interchangeably to refer to inhibitory, activating, or modulating molecules identified using assays of the invention. Inhibitors are compounds that, e.g., bind to, partially or totally block stimulation, decrease, prevent, delay activation, inactivate, desensitize, or down regulate GPR84 activity, e.g., antagonists. Activators are compounds that, e.g., bind to, stimulate, increase, open, activate, facilitate, enhance activation, sensitize, or up regulate GPR84 activity, e.g., agonists. Modulators also include compounds that, e.g., alter the interaction of a receptor with extracellular proteins that bind activators or inhibitors, G proteins, or kinases. Such assays for inhibitors and activators include, e.g., expressing GPR84, CD36 and $G_{qi9}$ in cells or cell membranes, applying putative modulator compounds and then determining the functional effects on taste transduction. Results of assays with potential activators, inhibitors, or modulators are compared to control samples without the inhibitor, activator, or modulator to examine the extent of modulation of GPR84 activity. Control samples (untreated with modulators) are assigned a relative GPR84 activity value of 100%. Inhibition of a GPR84 is achieved when the GPR84 activity value relative to the control is about 80%, optionally 50% or 25-0%. Activation of a GPR84 is achieved when the GPR84 activity value relative to the control is 110%, optionally 150%, optionally 200-500%, or 1000-3000% higher.

Thus, the invention provides assays for detecting and characterizing taste modulation, wherein GPR84 is used as a reporter molecule for determining the functional effect of modulators on fatty acid taste transduction. The phrase "functional effect(s)" in the context of assays for testing compounds that modulate GPR84 activity includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, $IP_3$, or intracellular $Ca^{2+}$)

By "determining the functional effect" in the context of assays herein is meant assays for a compound that increases or decreases a parameter that is indirectly or directly under the influence of GPR84, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties; patch clamping; voltage-sensitive dyes; whole cell currents; radioisotope efflux; inducible markers; ligand-binding assays; voltage, membrane potential and conductance changes; ion flux assays; changes in intracellular second messengers such as cAMP, cGMP, and inositol triphosphate ($IP_3$); changes in intracellular calcium levels; and the like.

Taste receptors bind tastants and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by $G_q$ and other cognate G proteins, and modulation of diverse channels by $G_i$ and other G proteins. Downstream consequences can also be examined such as generation of diacyl glycerol and $IP_3$ by phospholipase C, and in turn, for calcium mobilization by $IP_3$. Accordingly, in one embodiment, activation of GPR84 can be detected using monitoring changes in intracellular calcium by detecting FURA-2-dependent fluorescence in the host cell.

Activated GPCR receptors become substrates for kinases that phosphorylate the C-terminal tail of the receptor (and possibly other sites as well). Thus, activators can promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., Methods in Enzymology, vols. 237 and 238 (1994) and volume 96 (1983); Bourne, et al. (1991) Nature 10:349:117-27; Bourne, et al. (1990) Nature 348:125-32; Pitcher, et al. (1998) Annu. Rev. Biochem. 67:653-92.

As indicated, ion flux assays can be carried out to determine whether a compound modulated GPR84 activity. Changes in ion flux can be assessed by determining changes in ionic polarization (i.e., electrical potential) of the cell or membrane expressing a GPR84 protein. One means to determine changes in cellular polarization is by measuring changes in current (thereby measuring changes in polarization) with voltage-clamp and patch-clamp techniques (see e.g., Ackerman, et al. (1997) New Engl. J. Med. 336:1575-1595). Whole cell currents are conveniently determined using a standard. Other known assays include: radiolabeled ion flux assays and fluorescence assays using voltage-sensitive dyes (see, e.g., Vestergarrd-Bogind, et al. (1988) J. Membrane Biol. 88:67-75; Gonzales & Tsien (1997) Chem. Biol. 4:269-277; Daniel, et al. (1991) J. Pharmacol. Meth. 25:185-193; Holevinsky, et al. (1994) J. Membrane Biology 137:59-70). Generally, the compounds to be tested are present in the range from 1 pM to 100 mM.

The effects of the test compounds upon the function of GPR84 can be measured by examining any of the parameters described above. Any suitable physiological change that affects GPCR activity can be used to assess the influence of a test compound on GPR84. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that can be employed are those disclosed in the Molecular Probes 1997 Catalog.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen, et al. (1991) Proc. Natl Acad. Sci. USA 88:9868-9872 and Dhallan, et al. (1990) Nature 347:184-187). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, musearinic acetylcholine receptors, dopamine receptors, serotonin receptors, and the like), which, when activated, causes a change in cyclic nucleotide levels in the cytoplasm.

In addition, the uptake of fluorescently labeled fatty acids via CD36 can be used as an indication of activity. Such an assay is commercially available from sources such as Molecular Devices (Sunnyvale, Calif.) for use with FLIPR.

Non-human animals expressing GPR84, can also be used for receptor assays. Such expression can be used to determine whether a test compound specifically binds to a mammalian taste transmembrane receptor polypeptide in vivo by contacting a non-human animal stably or transiently transfected with a nucleic acid molecule of the invention with a test compound and determining whether the animal reacts to the test compound by specifically binding to the receptor polypeptide.

Animals transfected or infected with the vectors of the invention are particularly useful for assays to identify and characterize tastants/ligands that can bind to a specific or sets of receptors. Such vector-infected animals expressing human chemosensory receptor sequences can be used for in vivo screening of tastants and their effect on, e.g., cell physiology (e.g., on taste neurons), on the CNS, or behavior.

Means to infect/express nucleic acids and vectors are well-known in the art. A variety of individual cell, organ, or whole animal parameters can be measured by a variety of means. The nucleic acid molecule of the invention can be for example expressed in animal taste tissues by delivery with an infecting agent, e.g., adenovirus expression vector.

The compounds tested as modulators of GPR84 can be any small chemical compound, or a biological entity, such as a protein, nucleic acid or lipid. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or ligand compounds). Such libraries are then screened in one or more assays, as described herein, to identify those library members (particular chemical species or subclasses) that display a desired characteristic activity. The compounds thus identified can serve as conventional "lead compounds" or can themselves be used as potential or actual therapeutics. GPR84 modulators identified in accordance with the present invention can be used in any food product, confectionery, pharmaceutical composition, or ingredient thereof to thereby modulate the taste of the product, composition, or ingredient in a desired manner.

What is claimed is:

1. An isolated nucleic acid molecule encoding CD36, $G_{qi9}$, and G protein-coupled receptor 84 (GPR84) proteins.

2. An expression vector comprising the nucleic acid molecule of claim 1.

3. The expression vector of claim 2, wherein expression of CD36, $G_{qi}9$, and GPR84 is inducible.

4. The expression vector of claim 2, wherein expression of CD36, $G_{qi}9$, and GPR84 is constitutive.

5. An isolated recombinant host cell which co-expresses CD36, $G_{qi9}$, and GPR84 proteins.

* * * * *